(12) United States Patent
Wang et al.

(10) Patent No.: US 10,400,173 B2
(45) Date of Patent: Sep. 3, 2019

(54) SILOXANE-MODIFIED CYCLOTRIPHOSPHAZENE HALOGEN-FREE FLAME RETARDANT, PREPARATION PROCESS AND USE THEREOF

(71) Applicant: Shengyi Technology Co., Ltd., Guangdong (CN)

(72) Inventors: Yongzhen Wang, Guangdong (CN); Yueshan He, Guangdong (CN); Zhongqiang Yang, Guangdong (CN); Yongjing Xu, Guangdong (CN)

(73) Assignee: SHENGYI TECHNOLOGY CO., LTD., Guangdong (CN)

( * ) Notice: Subject to any disclaimer, the term of this patent is extended or adjusted under 35 U.S.C. 154(b) by 228 days.

(21) Appl. No.: 15/475,471

(22) Filed: Mar. 31, 2017

(65) Prior Publication Data
US 2018/0112133 A1    Apr. 26, 2018

(30) Foreign Application Priority Data

Oct. 20, 2016 (CN) .......................... 2016 1 0915852

(51) Int. Cl.

| | | |
|---|---|---|
| C08K 5/544 | (2006.01) | |
| C09K 21/12 | (2006.01) | |
| B32B 15/092 | (2006.01) | |
| B32B 27/20 | (2006.01) | |
| B32B 37/06 | (2006.01) | |
| C08J 5/24 | (2006.01) | |
| C08K 3/22 | (2006.01) | |
| C08K 3/36 | (2006.01) | |
| C07F 9/659 | (2006.01) | |
| C08K 5/5399 | (2006.01) | |
| C08K 5/54 | (2006.01) | |
| C08L 27/02 | (2006.01) | |
| D06M 15/673 | (2006.01) | |

(52) U.S. Cl.
CPC ............ *C09K 21/12* (2013.01); *B32B 15/092* (2013.01); *B32B 27/20* (2013.01); *B32B 37/06* (2013.01); *C07F 9/659* (2013.01); *C08J 5/24* (2013.01); *C08K 3/22* (2013.01); *C08K 3/36* (2013.01); *C08K 5/5399* (2013.01); *C08K 5/5406* (2013.01); *C08K 5/5442* (2013.01); *C08L 27/02* (2013.01); *D06M 15/673* (2013.01); *B32B 2305/076* (2013.01); *B32B 2307/3065* (2013.01); *B32B 2383/00* (2013.01); *C08J 2363/00* (2013.01); *C08J 2363/04* (2013.01); *C08K 2003/2206* (2013.01); *C08K 2003/2227* (2013.01); *C08L 2201/02* (2013.01)

(58) Field of Classification Search
CPC . C09K 21/12; C08K 3/22; C08K 3/26; C08K 5/5442; C08K 2003/2206; C08K 2003/2227; C08J 5/24; C08J 2363/04; B32B 15/092; B32B 27/20; B32B 37/06; B32B 2283/00; B32B 2305/076; B32B 2307/3065

See application file for complete search history.

(56) References Cited

U.S. PATENT DOCUMENTS 4,405,738 A    9/1983 McNeely

FOREIGN PATENT DOCUMENTS

| CN | 101993456 A | 3/2011 | |
|---|---|---|---|
| CN | 102199294 A | 9/2011 | |
| CN | 102250147 A | 11/2011 | |
| CN | 103435652 A | 12/2013 | |
| CN | 104262399 A | 1/2015 | |
| CN | 104478934 A | 4/2015 | |
| CN | 104877173 A * | 9/2015 | ............ C07F 9/6593 |

OTHER PUBLICATIONS

Qian, et al.: "The non-halogen flame retardant epoxy resin based on a novel compound with phosphaphenanthrene and cyclotriphosphazene double functional groups", J. Polymenr Degradation and Stability 96 (2011), pp. 1118-1124.
Schaefer, et al: "Synthesis and Properties of Flame-Retardant Epoxy Resins Based on DOPO and One of Its Analog DPPO", J. of Applied Polymer Science 105 (2007), pp. 685-696.
Takahito, et al.: "Enhancement of thermal stability of polystyrene and poly(methyl methacrylate) by cyclotriphosphazene derivatives", J. Polymer Degradation and Stability 84 (2004), pp. 87-93.
Xia, et al.: "Synthesis of Novel Phosphorous-Containing Biphenol, 2-(5, 5-Dimethyl-4-phenyl-2-oxy-1,3,2-dioxaphosphorin-6-yl)-1,4-benzenediol and Its Application as Flame-Retardant in Epoxy Resin", J. of Applied Polymer Science 102 (2006), pp. 3842-3847.
Yang, et al.: "Synthesis, mechanical properties and fire behaviors of rigid polyurethane foam with a reactive flame retradant containing phosphazene and phosphate", J. Polyment Degradation and Stability 122 (2015), pp. 102-189.

* cited by examiner

*Primary Examiner* — Bijan Ahvazi
(74) *Attorney, Agent, or Firm* — Norton Rose Fulbright US LLP

(57) ABSTRACT

The present invention provides a siloxane-modified cyclotriphosphazene halogen-free flame retardant, and a preparation method and a use thereof. The siloxane-modified cyclotriphosphazene halogen-free flame retardant has the structural formula as shown in Formula I. In the siloxane-modified cyclotriphosphazene halogen-free flame retardant of the present invention, three kinds of structures of siloxane, aryl phosphorus oxygen compound and cyclotriphosphazene are built in one molecular formula, which combines the advantages of three structures, improves the compatibility between the flame retardant and resins, has a high flame retardant efficiency and a better char formation and can greatly increase the flame retardancy and stability of resin cured products.

22 Claims, No Drawings

SILOXANE-MODIFIED CYCLOTRIPHOSPHAZENE HALOGEN-FREE FLAME RETARDANT, PREPARATION PROCESS AND USE THEREOF

This application claims priority under Section 119 from Chinese Patent Application No. 201610915852.2 filed on Oct. 20, 2016, which is hereby incorporated by reference in its entirety.

TECHNICAL FIELD

The present invention belongs to the technical field of flame retardant materials, particularly relates to a siloxane-modified cyclotriphosphazene halogen-free flame retardant, a preparation process and a use thereof.

BACKGROUND ART

Due to the advantages of non-toxicity, low smoke density and low moisture absorption, cyclotriphosphazene flame retardants are generally used for flame-retarding modification of materials, such as epoxy resins, unsaturated resins, polyurethanes, cyanates, benzoxazines and the like. In order to increase the flame retardant efficiency of cyclotriphosphazene flame retardants, cyclotriphosphazene-functional groups and 9,10-dihydro-9-oxa-10-phosphaphenanthrene-10-oxide (DOPO) or dioxacyclophosphate are generally integrated into the same flame retardant molecules to form synergistic flame retardants. Phosphorus elements in phosphaphenanthrene or phosphate play a role through gas-phase flame-retardant mechanism and mechanism of catalytic char formation together with cyclotriphosphazene intumescent flame retardant mechanism, so as to improve the flame retardant efficiency of the flame retardants, to reduce the usage amount of flame retardants and to give the materials excellent overall performance.

The document (Muraki, T., et al. Polymer Degradation and Stability. 2004, 84(1):87-93), CN104478934A and U.S. Pat. No. 4,405,738(A) all disclose that cyclotriphosphazene flame retardants containing dioxacyclophosphate have an obviously improved flame-retarding efficiency as compared to cyclotriphosphazene flame retardants. The aforesaid documents all show that the combinations of phosphates with cyclotriphosphazene flame retardants are advantageous to increasing the flame-retarding efficiency of flame retardants. However, phosphate groups having a bad thermal resistance are independently bonded to the end of the flame retardant, and water absorption is too great, which are not conducive to the application of such flame retardants in the fields of CCL which have higher performance requirements on heat, water absorption and the like.

CN101993456A and CN104262399A disclose gradually replacing phosphates with DOPO structures having better thermal resistance and lower water absorption for the preparation of flame retardants containing cyclotriphosphazene and phosphaphenanthrene at the same time. CN103435652A further discloses a process for preparing a novel compound having high nitrogen content and containing phosphaphenanthrene and phosphazene double functional groups. Although the flame-retarding efficiency of these flame retardants is obviously improved, high density accumulation of aromatic groups in flame retardant molecules results in an extremely low dissolving property of such flame retardants in common low-boiling solvents such as butanone, acetone, toluene, ethylene glycol methyl ether, propylene glycol monomethyl ether. Such flame retardants can only be dissolved by adding a larger volume of strong polar organic solvents, such as N,N-dimethylformamide, N,N-diethylacetamide and dimethylsulfoxide. These solvents having a high boiling point bring much trouble to the subsequent processing. High density accumulation of aromatic groups also renders undesirable compatibility of flame retardants in resin systems. As compared to common micromolecular cyclotriphosphazene flame retardants, it tends to agglomerate and precipitate in the resin after the solvent is removed, which not only is not conducive to improving the flame-retardant property of resins, but also leads to uneven structures of resins in the molding process, so as to affect the overall performance of the resins.

Meanwhile, the cyclotriphosphazene flame retardants containing a phosphaphenanthrene structure currently disclosed have a melting point of generally about 160 to 200° C. Therefore, when the flame-retardant modified products by using such flame retardants are subject to heat processing, such as drilling, soldering and the like, the flame retardant readily melts and precipitates, resulting in product defects such as dried flowers, hollow and the like, which are seriously threats to the product life.

CN102199294A discloses a hyperbranched polysiloxane and a process for preparing the same, wherein said hyperbranched polysiloxane contains both a phosphaphenanthrene structure and an organosilicon epoxy resin. Although it has a better compatibility in resin systems, its flame-retardant property needs to be further improved. Moreover, its hyperbranched structure is more complex.

CN102250147A discloses a process for preparing cyclotriphosphazene containing silicon functional group, and a use thereof. The cyclotriphosphazene containing silicon functional group contains both cyclotriphosphazene and siloxane structure. Although polypropylene obtained by applying such flame retardant into polypropylene systems has a higher elongation at break, its oxygen index is only about 25%, and the flame retardancy is still to be further improved.

Accordingly, it is desirable in the art to obtain a halogen-free flame retardant which is capable of both enhancing the flame-retardant property and improving its compatibility in resin systems.

DISCLOSURE OF THE INVENTION

In view of the shortcomings of the prior art, the object of the present invention is to provide a siloxane-modified cyclotriphosphazene halogen-free flame retardant, a process for preparing the same and a use thereof. The halogen-free flame retardant of the present invention combines three kinds of structures of siloxane, aryl phosphorus oxygen structure and cyclotriphosphazene, and has good thermal stability, high char formation rate and excellent flame retardant efficiency, and has excellent compatibility with resin systems.

In order to achieve such object, the present application discloses the following technical solution.

On one side, the present invention provides a siloxane-modified cyclotriphosphazene halogen-free flame retardant, characterized in that the flame retardant has the structural formula as shown in Formula I:

Formula I

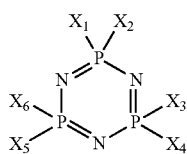

wherein the groups of $X_1$-$X_6$ are each independently selected from

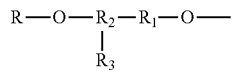

or —O—R', and at least two groups therein are

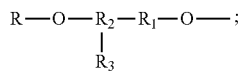

$R_1$ is a substituted or unsubstituted arylene; $R_2$ is selected from the group consisting of methenyl,

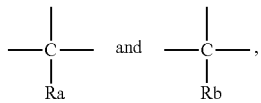

wherein $R_a$ is a substituted or unsubstituted C1-C5 alkyl group; $R_b$ is a substituted or unsubstituted aryl group; $R_3$ is a group containing aryl phosphorus oxygen structure; Rs in the groups of $X_1$-$X_6$ is independently selected from siloxane group or hydrogen, and Rs in the groups of $X_1$-$X_6$ are not hydrogen at the same time; R' is a substituted or unsubstituted aryl group.

In the present invention, each phosphorus atom in the structure of cyclotriphosphazene

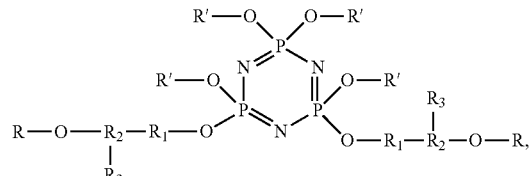

can connect to two groups. Thus such structure can connect to six groups altogether, wherein at least two of said six groups are

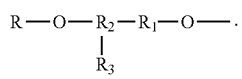

Moreover, Rs in said six groups are not hydrogen at the same. That is to say, it should be ensured that at least one of the six groups is bonded to the siloxane group.

In the present invention, the typical but nonrestrictive structure of Formula I is anyone selected from the group consisting of

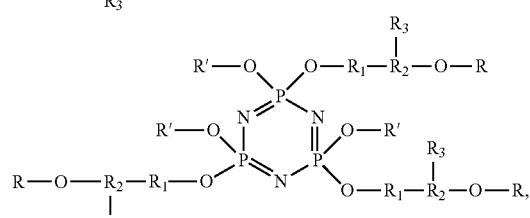

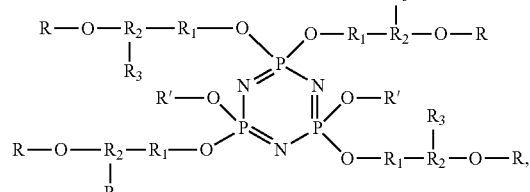

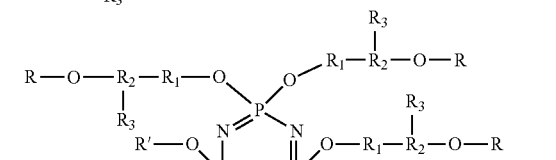

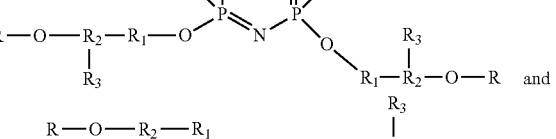

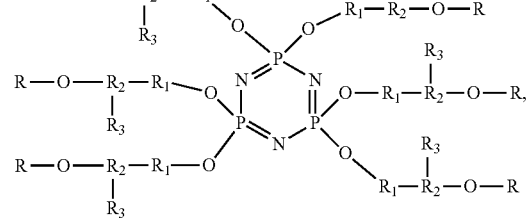

or a combination of at least two selected therefrom.

Preferably, $R_1$ is anyone selected from the group consisting of

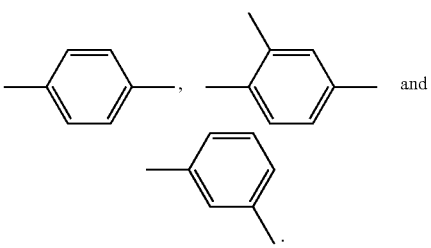

In the present invention, $R_a$ is a substituted or unsubstituted C1-C5 alkyl group, e.g. a substituted or unsubstituted C1, C2, C3, C4, or C5 alkyl group. Preferably, $R_a$ is methyl.

In the present invention, $R_b$ is a substituted or unsubstituted aryl group, e.g. a substituted or unsubstituted phenyl group, a substituted or unsubstituted naphthyl group, or a substituted or unsubstituted pyridyl group. Preferably, $R_b$ is phenyl.

Preferably, $R_3$ is anyone selected from the group consisting of

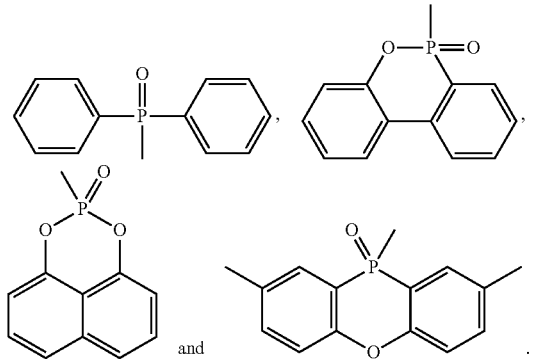

Preferably, the siloxane group is anyone selected from the group consisting of

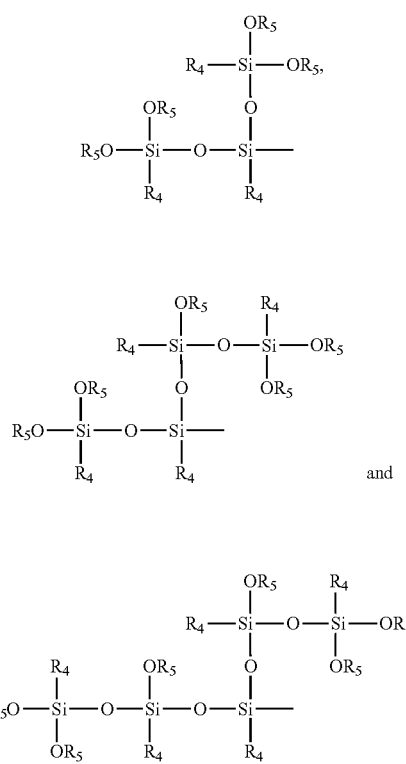

or a combination of at least two selected therefrom, wherein $R_4$ is anyone selected from the group consisting of

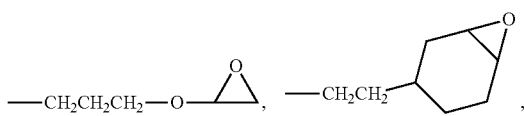

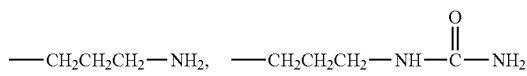

and —CH$_2$CH$_2$CH$_2$—NH—CH$_2$CH$_2$—NH$_2$; $R_5$ is selected from C1-C5 alkyl groups, preferably methyl or ethyl.

Preferably, R' is anyone selected from the group consisting of substituted or unsubstituted phenyl, substituted or unsubstituted naphthyl, substituted or unsubstituted alkylphenyl, substituted or unsubstituted cycloalkylphenyl, substituted or unsubstituted nitrophenyl, substituted or unsubstituted nitrogen-containing heterocyclylphenyl, substituted or unsubstituted aryloxyphenyl, or a combination of at least two selected therefrom. Said combination in the present invention means that, when at least two of $X_1$-$X_6$ groups are —O—R', R' is selected from the aforesaid different groups. For example, when $X_1$ and $X_3$ are —O—R', R' in $X_1$ and $X_3$ can be selected from the same groups above (e.g. substituted or unsubstituted phenyl group at the same time), or from the different groups above (e.g. one may be a substituted or unsubstituted phenyl group, and the other may be a substituted or unsubstituted naphthyl group). When only one group in $X_1$-$X_6$ groups is —O—R', said combination means that the siloxane-modified cyclotriphosphazene halogen-free flame retardant of the present invention is a combination of at least two compounds having the structure as shown in Formula I, wherein R' in said at least two compounds is selected from the different groups above.

Preferably, R' is anyone selected from the group consisting of,

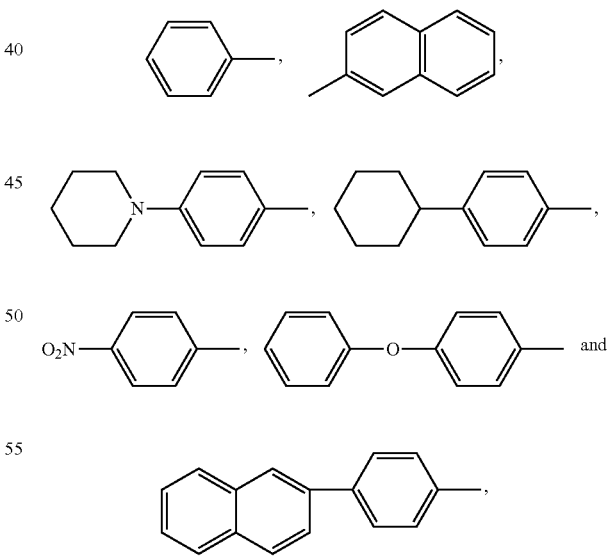

or a combination of at least two selected therefrom.

Preferably, the siloxane-modified cyclotriphosphazene halogen-free flame retardant of the present invention is anyone selected from the group of the compounds having the following formulae a-g, or a combination of at least two selected therefrom:

Formula a
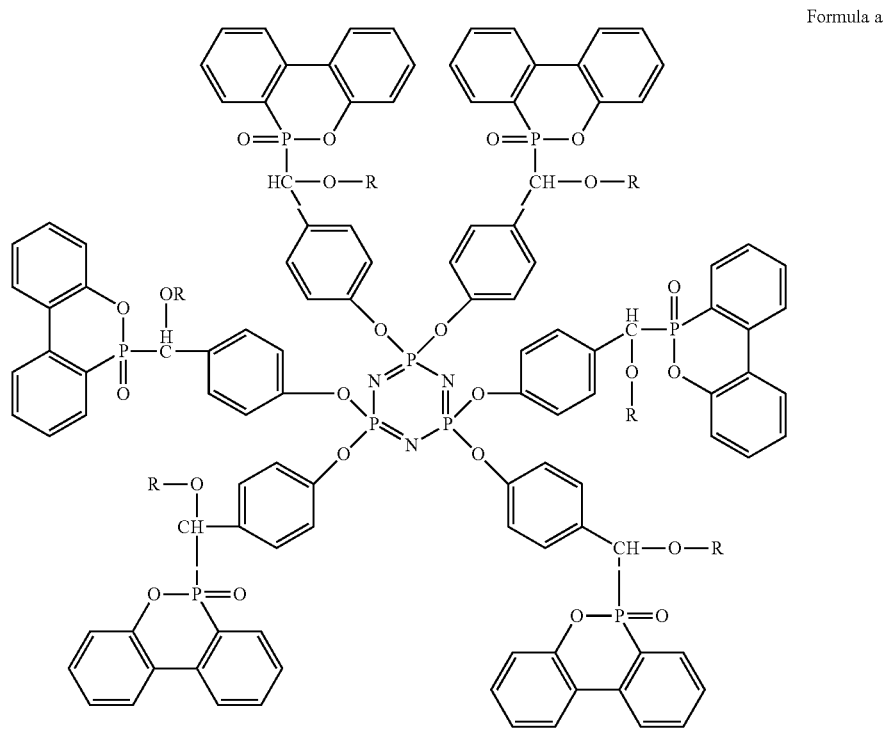
wherein six Rs in Formula a are each independently
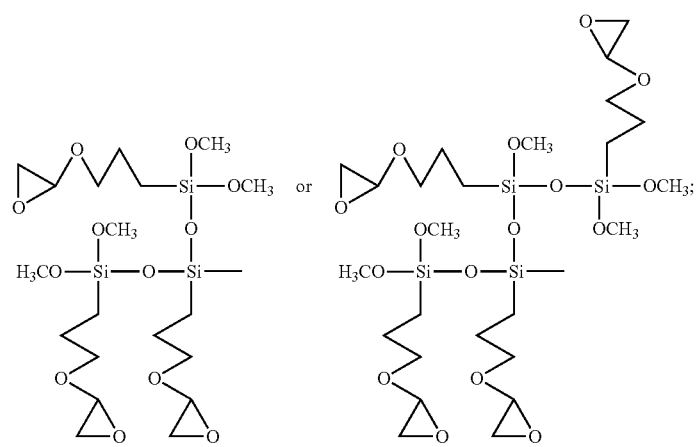
Formula b
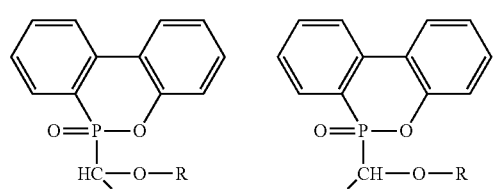

-continued
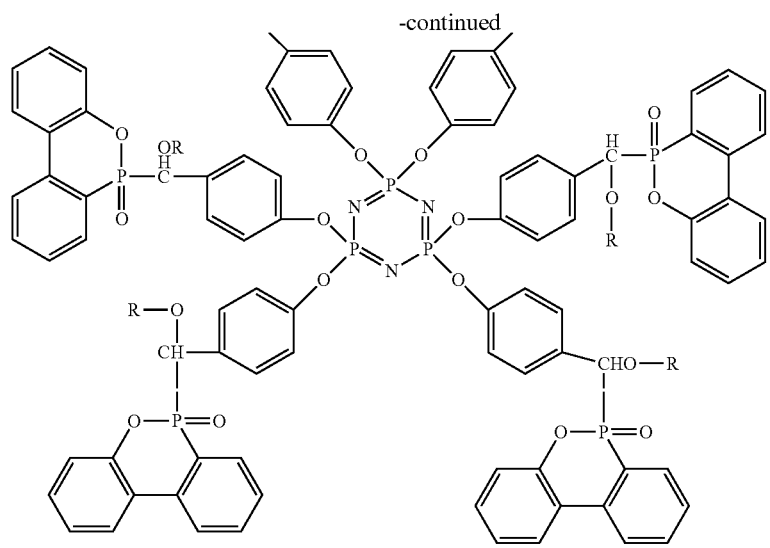
wherein six Rs in Formula b are each independently
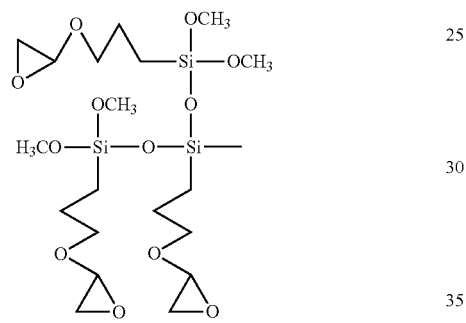
or H, but not H at the same time;
Formula c
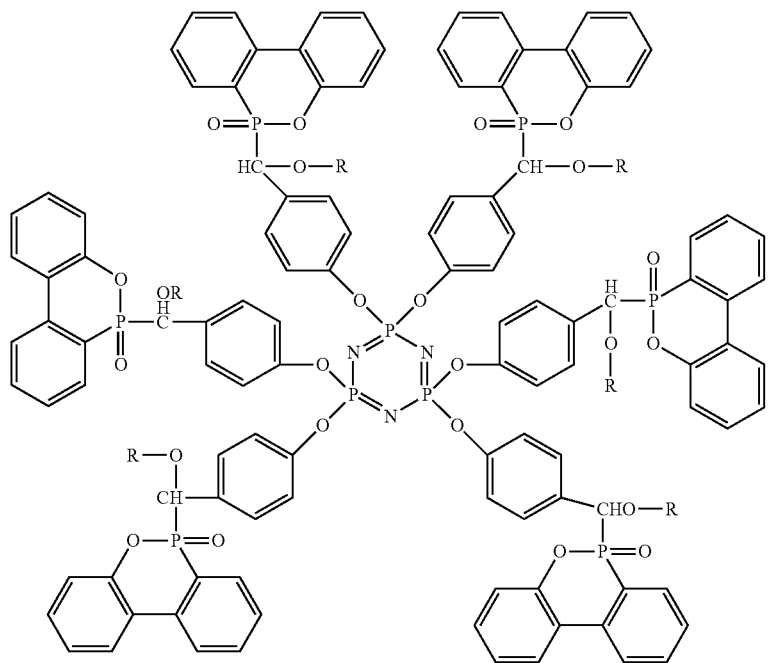

11
wherein six Rs in Formula c are each independently
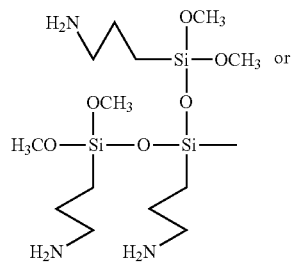 or
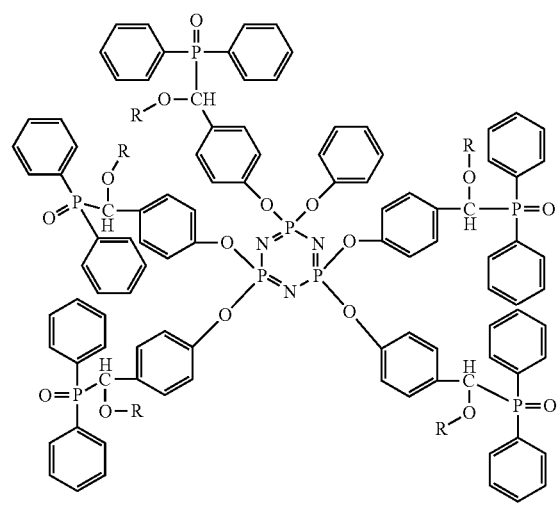
12
wherein six Rs in Formula d are each independently
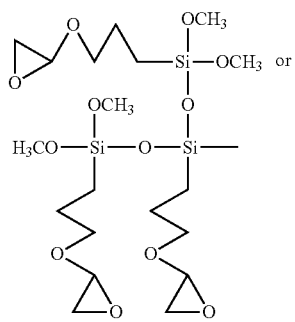 or
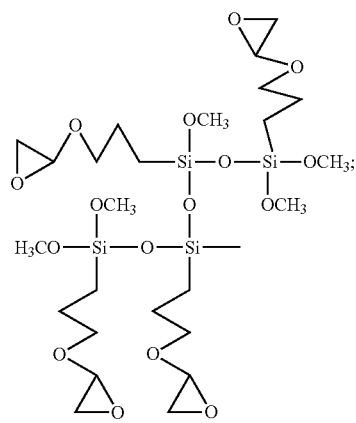
Formula d
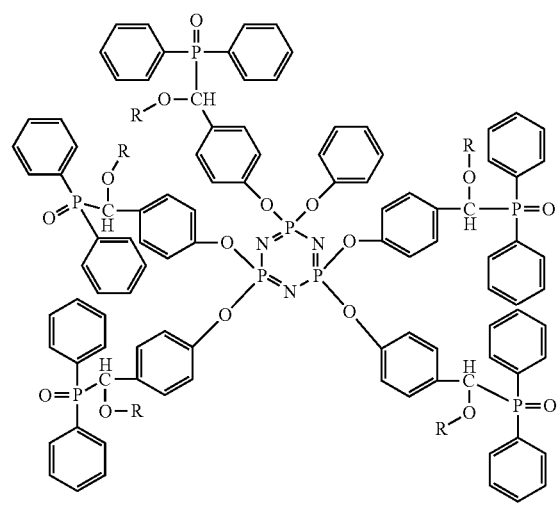
Formula e
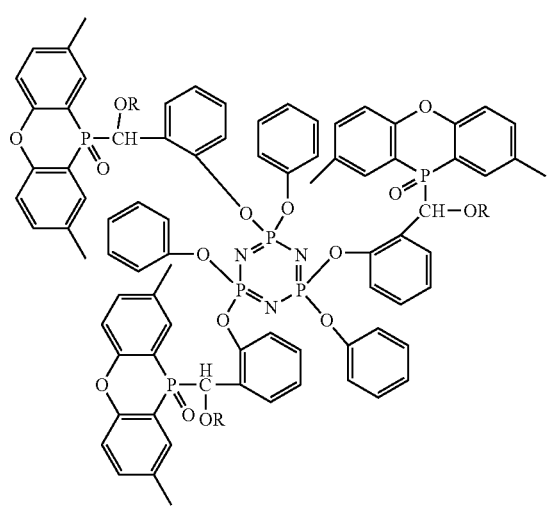

wherein Rs in Formula e are
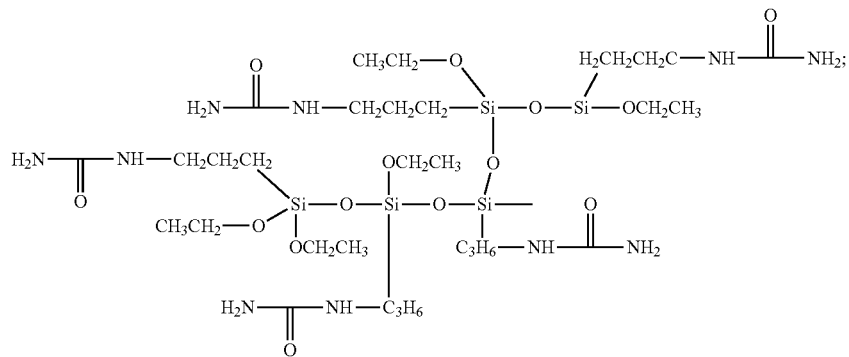
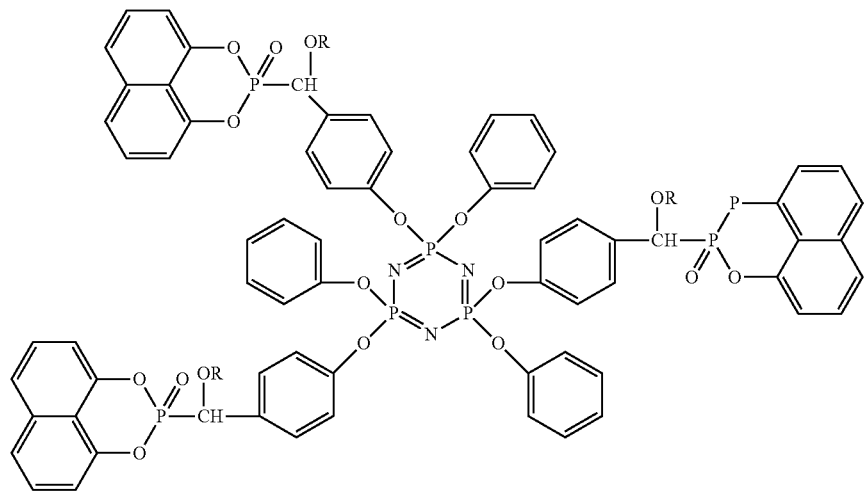
Formula f
wherein three Rs in Formula f are each independently
-continued
Formula g
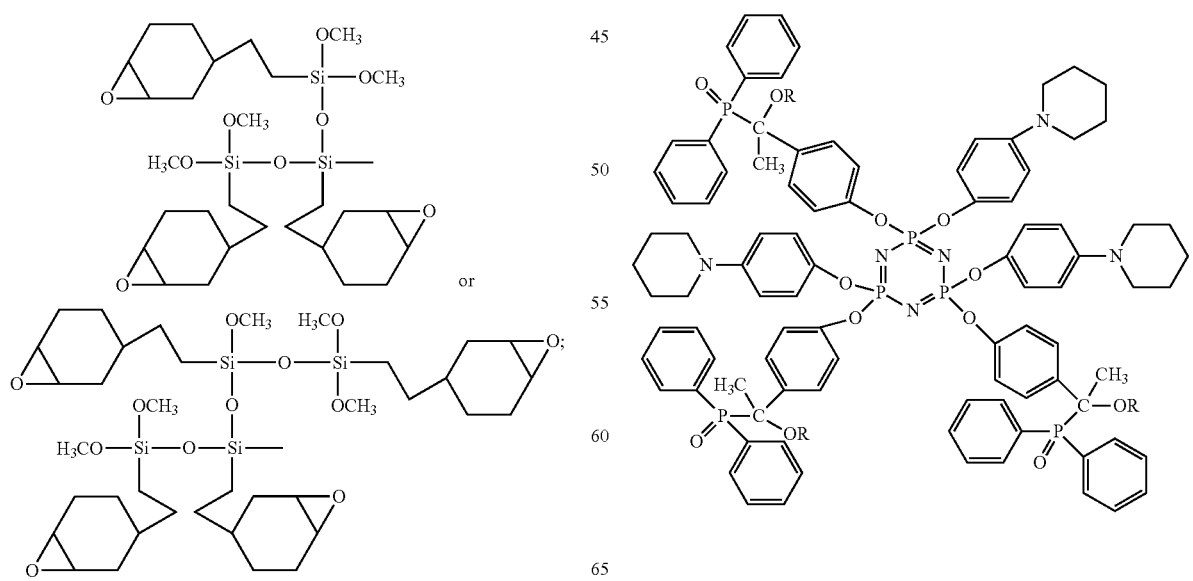

wherein three Rs in Formula g are each independently

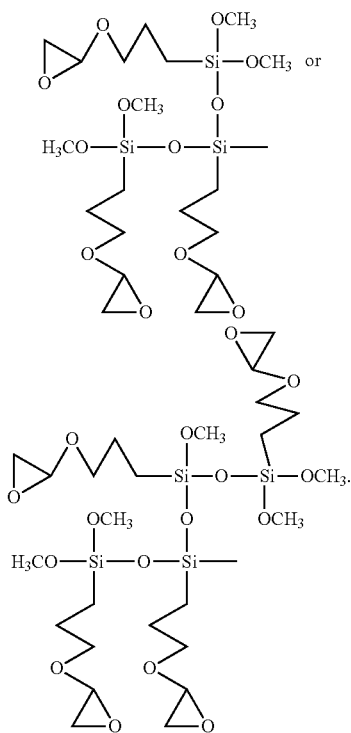

Since the present invention provides a halogen-free flame retardant, the aforesaid groups or substituents of groups contain no halogen.

The siloxane-modified cyclotriphosphazene halogen-free flame retardant of the present invention is a self-synergistic flame retardant having a synergistic effect between the structures of the cyclotriphosphazene, the phosphorus aromatic ring and the siloxane contained in the structural formula thereof, which is capable of synergistically enhancing the flame-retarding effect of the flame-retardant. Thus the resin cured product obtained by using in resin compositions has the advantages of good flame retardancy, good thermal stability and high char formation rate.

On the other side, the present invention provides a process for preparing the above siloxane-modified cyclotriphosphazene halogen-free flame retardant, comprising the following steps:

(1) reacting aldehyde- or keto-substituted aryl phenol shown in Formula II and any optional aryl phenol shown in Formula III with hexachlorocyclotriphosphazene to obtain the cyclotriphosphazene compound as shown in Formula IV, wherein the reaction formula is as follows:

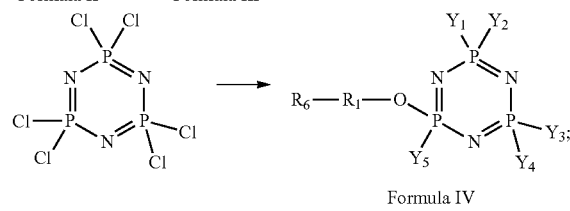

(2) reacting the cyclotriphosphazene compound as shown in Formula IV obtained in step (1) with phosphorus-containing aromatic compound containing P—H bonds as shown in Formula V to obtain the cyclotriphosphazene compound containing hydroxyl and aryl phosphorus oxygen structure as shown in Formula VI, wherein the reaction formula is as follows:

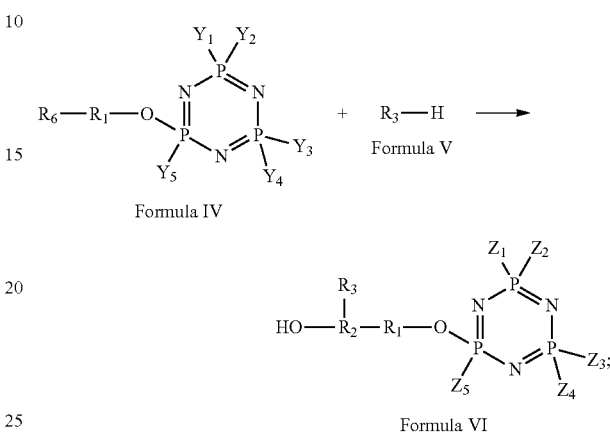

(3) reacting the cyclotriphosphazene compound containing hydroxyl and aryl phosphorus oxygen structure as shown in Formula VI obtained in step (2) with siloxane monomer as shown in Formula VII to obtain the siloxane-modified cyclotriphosphazene halogen-free flame retardant as shown in Formula I, wherein the reaction formula is as follows:

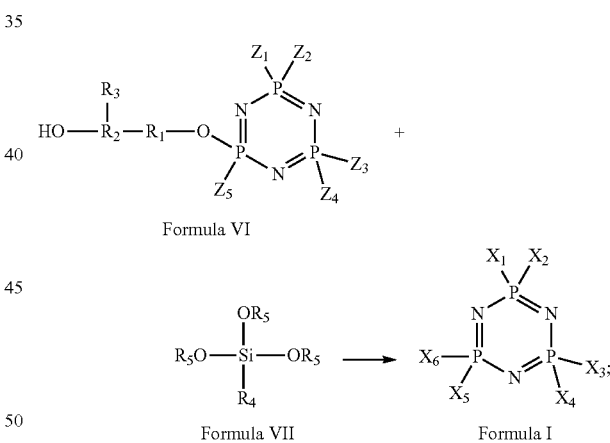

wherein the groups of $Y_1$-$Y_5$ are each independently selected from $R_6$—$R_1$—O or —O—R', and at least one is $R_6$—$R_1$—O:$R_1$ is a substituted or unsubstituted arylidene; $R_6$ is aldehyde group or

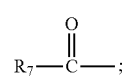

$R_7$ is a substituted or unsubstituted C1-C5 alkyl or a substituted or unsubstituted aryl; R' is a substituted or unsubstituted aryl; the groups of $Z_1$-$Z_5$ are each independently selected from

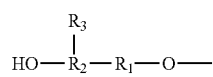

or —O—R', and at least one is

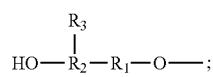

$R_2$ is selected from the group consisting of methenyl,

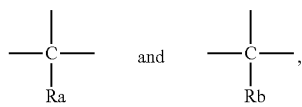

wherein $R_a$ is a substituted or unsubstituted C1-C5 alkyl; $R_b$ is a substituted or unsubstituted aryl; $R_3$ is a group containing aryl phosphorus oxygen structure; the groups of $X_1$-$X_6$ are each independently selected from

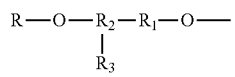

or —O—R', and at least two groups are

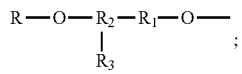

$R_4$ is selected from the group consisting of

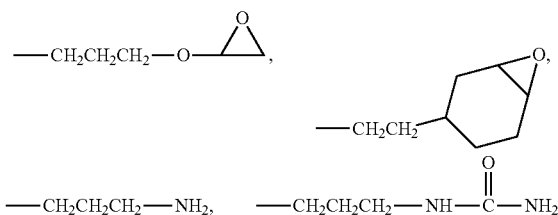

and —$CH_2CH_2CH_2$—NH—$CH_2CH_2$—$NH_2$; $R_5$ is selected from the group consisting of C1-C5 alkyl groups; R' is a substituted or unsubstituted aryl; Rs in $X_1$-$X_6$ are independently selected from siloxane group or hydrogen, and Rs in $X_1$-$X_6$ are not hydrogen at the same time.

According to the preparation process above, it can be seen that said siloxane group is obtained by reacting the cyclotriphosphazene compound containing hydroxyl and aryl phosphorus oxygen structure as shown in Formula VI in step (3) with siloxane monomer as shown in Formula VII. In the cyclotriphosphazene compound containing hydroxyl and aryl phosphorus oxygen structure as shown in Formula VI, there may be some hydroxyl groups which do not participate in the reaction, so that some hydroxyl groups are retained. However, it shall be ensured as far as possible in the reaction that at least one hydroxyl group is replaced by siloxane groups.

Preferably, the siloxane group is anyone selected from the group consisting of

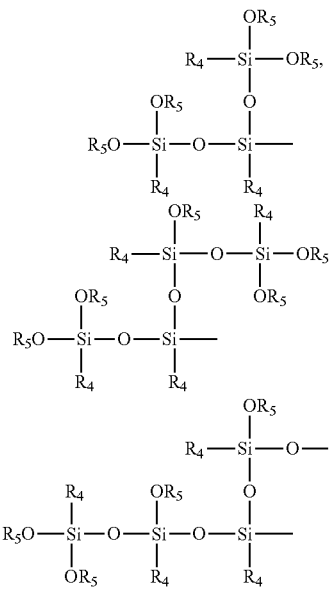

or a combination of at least two selected therefrom, wherein $R_4$ is anyone selected from the group consisting of

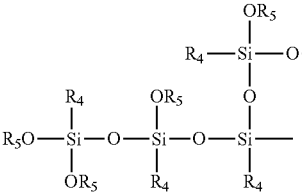

and —$CH_2CH_2CH_2$—NH—$CH_2$—$CH_2$—$NH_2$; $R_5$ is selected from C1-C5 alkyl groups, preferably methyl or ethyl.

In the present invention, $R_7$ is a substituted or unsubstituted C1-C5 alkyl group. That is to say, $R_7$ may be a substituted or unsubstituted C1, C2, C3, C4 or C5 alkyl group, preferably a methyl group. said $R_7$ is a substituted or unsubstituted aryl group. That is to say, $R_7$, may be a substituted or unsubstituted phenyl group, a substituted or unsubstituted naphthyl group or a substituted or unsubstituted pyridyl group. Preferably, $R_7$ is a phenyl group.

In the present invention, the siloxane, aryl phosphorus oxygen structure and cyclotriphosphazene structure are simultaneously built in a halogen-free flame retardant molecule through a three-step reaction. The good flexibility of the siloxane is used to improve the compatibility between the flame retardant molecule and the resin. The terminal epoxy groups or terminal amino groups on the siloxane are involved in the reaction, which can minimize the precipitation of the flame retardant in the cross-linking and curing of resins. Meanwhile, the flame-retardant performance of siloxane further improves the efficiency of the flame retardant, and realizes the high-efficiency flame retardant of the modified cyclotriphosphazene compound.

In step (1) of the preparation process of the present invention, the aldehyde- or keto-substituted aryl phenol shown in Formula II and aryl phenol shown in Formula III can react with hexachlorocyclotriphosphazene, or only the aldehyde- or keto-substituted aryl phenol shown in Formula II can react with hexachlorocyclotriphosphazene.

Preferably, during the reaction of the mixture of aldehyde- or keto-substituted aryl phenol shown in Formula II and aryl phenol shown in Formula III with hexachlorocyclotriphosphazene in step (1), the aldehyde- or keto-substituted aryl phenol shown in Formula II and aryl phenol shown in Formula III are in a molar ratio of 1:2-10:1, e.g. 1:2, 1:1.5, 1:1, 2:1, 3:1, 4:1, 5:1, 6:1, 7:1, 8:1, 9:1 or 10:1.

Preferably, in step (1), the two of the aldehyde- or keto-substituted aryl phenol shown in Formula II and aryl phenol shown in Formula III and hexachlorocyclotriphosphazene are in a molar ratio of 6.1:1-7.1:1, e.g. 6.1:1, 6.2:1, 6.3:1, 6.4:1, 6.5:1, 6.6:1, 6.7:1, 6.8:1, 7:1 or 7.1:1, preferably 6.3:1-6.6:1.

Preferably, during the reaction of the mixture of aldehyde- or keto-substituted aryl phenol shown in Formula II and aryl phenol shown in Formula III with hexachlorocyclotriphosphazene in step (1), the aldehyde- or keto-substituted aryl phenol shown in Formula II and aryl phenol shown in Formula III are in a molar ratio of 2:4-6:0.

Preferably, the aldehyde- or keto-substituted aryl phenol shown in Formula II in step (1) is anyone selected from the group consisting of

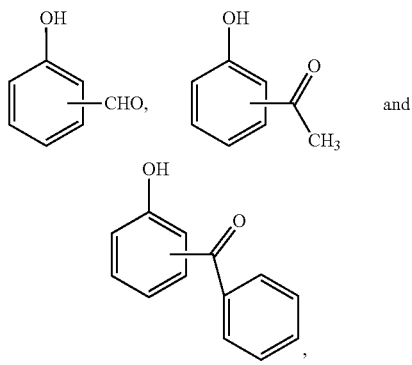

or a combination of at least two selected therefrom.

Preferably, the aryl phenol shown in Formula III in step (1) is anyone selected from the group consisting of

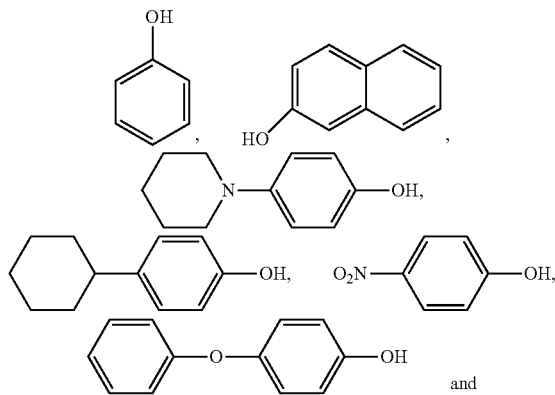

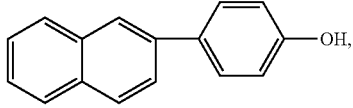

or a combination of at least two selected therefrom.

Preferably, the reaction in step (1) is carried out in an aprotic organic solvent having a boiling point of lower than 105° C., wherein the aprotic organic solvent is preferably anyone selected from the group consisting of dioxane, tetrahydrofuran, acetonitrile, acetone, butanone and ethyl acetate, or a combination of at least two selected therefrom.

Preferably, the reaction in step (1) is carried out in a reflux for 20-36 h, e.g. 20, 22, 24, 26, 28, 30, 32, 34 or 36 h.

Preferably, the aldehyde- or keto-substituted aryl phenol shown in Formula II and any optional aryl phenol shown in Formula III are reacted with an acid-binding agent at room temperature before the reaction in step (1) for 1-5 h, e.g. 1, 1.5, 2, 2.5, 3, 3.5, 4, 4.5 or 5 h.

Preferably, the acid-binding agent is anyone selected from the group consisting of dried sodium hydride, triethylamine, sodium carbonate, sodium hydrogencarbonate, potassium carbonate, potassium bicarbonate and pyridine.

Preferably, the acid-binding agent and the aldehyde- or keto-substituted aryl phenol shown in Formula II and any optional aryl phenol shown in Formula III are in a molar ratio of 1.1:1-1.3:1, e.g. 1.1:1, 1.2:1 or 1.3:1.

In the present invention, the crude product of the cyclotriphosphazene compound of Formula IV prepared in step (1) can be recrystallized by using a mixed solvent, filtrated, vacuum-dried at 50 to 75° C. (e.g. 50° C., 55° C., 60° C., 65° C., 70° C. or 75° C.) for 12-24 h (e.g. 12, 14, 16, 18, 20, 22 or 24 h) to obtain a white to gray crystalline cyclotriphosphazene compound. Preferably, the mixed solvent is a mixed solvent of ethyl acetate and tetrahydrofuran formulated in a volume ratio of 1:1-5:1 (e.g. 1:1, 1.5:1, 2:1, 2.5:1, 3:1, 3.5:1, 4:1, 4.5:1 or 5:1).

Preferably, the phosphorus-containing aromatic compound containing P—H bonds as shown of Formula V in step (2) is anyone selected from the group consisting of diphenylphosphine oxide (shortened as BPP), 9,10-dihydro-9-oxa-10-phosphaphenanthrene-10-oxide (shortened as DOPO), 1,8-dinaphthyl-1,3,2-dioxaphosphine (shortened as NDPO) and 9,10-dihydro-9-oxa-10-phosphaanthracene-10-oxide (shortened as DPPO), or a combination of at least two selected therefrom.

Preferably, in step (2), the cyclotriphosphazene compound of Formula IV and the phosphorus-containing compound containing P—H bonds of Formula V have a molar ratio of 1:2-1:6.3, e.g. 1:2, 1:2.5, 1:2.8, 1:3, 1:3.3, 1:3.5, 1:3.8, 1:4, 1:4.3, 1:4.5, 1:5, 1:5.5, 1:5.8, 1:6 or 1:6.3.

Preferably, the reaction in step (2) is carried out in an aprotic organic solvent having a boiling point of higher than 150° C., which is preferably N,N-dimethylformamide.

Preferably, the reaction temperature in step (2) ranges from 130-175° C., e.g. 130° C., 135° C., 140° C., 145° C., 150° C., 155° C., 160° C., 165° C., 170° C. or 175° C.

Preferably, the reaction in step (2) lasts for 8-20 h, e.g. 8, 9, 10, 12, 14, 15, 16, 18 or 20 h.

In the present invention, the crude product of the cyclotriphosphazene compound containing hydroxy and aryl phosphorus oxygen structure of Formula VI obtained in the step (2) can be washed three times under ultrasonic conditions in a mixed solvent of ethanol and ethyl acetate, and vacuum-dried at 60-80° C. (e.g. 60° C., 65° C., 70° C., 75° C. or 80° C.) for 24 hours to obtain a white to gray product.

Preferably, the siloxane monomer of Formula VII in step (3) is anyone selected from the group consisting of γ-(2,3-epoxypropoxy)propyltrimethoxysilane, γ-(2,3-epoxypropoxy)propyltriethoxysilane, 2-(3,4-epoxycyclohexyl)ethyltriethoxysilane, 3-ureidopropyltriethoxysilane, γ-aminopropyltriethoxy-silane and N-(2-aminoethyl)-3-aminopropyltriethoxysilane, or a combination of at least two selected therefrom.

Preferably, the cyclotriphosphazene compound containing hydroxyl and aryl phosphorus oxygen structure as shown in Formula VI and the siloxane monomer as shown in Formula VII have a molar ratio of 1:1-4:1, e.g. 1:1, 1.3:1, 1.5:1, 1.8:1, 2:1, 2.2:1, 2.5:1, 2.8:1, 3:1, 3.3:1, 3.5:1, 3.8:1 or 4:1.

Preferably, the reaction in step (3) is carried out in the presence of a catalyst.

Preferably, the catalyst is anyone selected from the group consisting of zinc isooctanoate, dibutyltin dilaurate, iron isooctanoate, manganese isooctanoate, cobalt isooctanoate, zirconium isooctanoate, cobalt acetylacetonate and copper acetylacetonate, or a combination of at least two selected therefrom.

Preferably, the catalyst is used in an amount of 0.1-0.8%, preferably 0.3-0.5% by mass of the siloxane monomer as shown in Formula VII.

Preferably, the step (3) is carried out in the presence of deionized water.

Preferably, the deionized water and the siloxane groups in the siloxane monomer as shown in the Formula VII have a molar ratio of 0.7:1-1.3:1, e.g. 0.7:1, 0.8:1, 0.9:1, 1:1, 1.2:1 or 1.3:1. The addition of deionized water promotes the conversion of the alkoxy groups attached to the silicon atoms in the siloxane monomer of Formula VII to silanol groups and promotes the polymerization of the siloxane monomer, so as to provide siloxane groups in the flame retardant structure of the present invention.

Preferably, the reaction in step (3) is carried out at 70-90° C. (e.g. 70° C., 73° C., 75° C., 78° C., 80° C., 85° C., 88° C. or 90° C.) for 5-7 h (e.g. 5, 5.3, 5.5, 5.8, 6, 6.5, 6.8 or 7 h), and continues at 110-1400 (e.g. 110° C., 115° C., 120° C., 125° C., 130° C., 135° C. or 140° C.) for 3-5 h (e.g. 3, 3.5, 4, 4.5 or 5 h).

Preferably, the reactions in steps (1)-(3) are carried out in the presence of a protecting gas. Preferably, the protecting gas is nitrogen.

On the other side, the present invention provides a halogen-free flame retardant resin composition comprising the siloxane-modified cyclotriphosphazene halogen-free flame retardant as stated above.

Preferably, the siloxane-modified cyclotriphosphazene halogen-free flame retardant is in an amount of 10-22%, e.g. 10%, 12%, 14%, 16%, 18%, 20% or 22%, by weight of the halogen-free flame retardant resin composition.

Preferably, the halogen-free flame retardant resin composition further comprises other thermosetting resins, which are thermosetting resins other than the siloxane-modified cyclotriphosphazene above.

Preferably, the other thermosetting resin is anyone selected from the group consisting of epoxy resin, unsaturated resin, polyurethane, cyanate resin and benzoxazine resin, or a combination of at least two selected therefrom.

Preferably, the halogen-free flame retardant resin composition further comprises a curing agent.

Preferably, the curing agent is anyone selected from the group consisting of phenolic curing agent, amine curing agent, anhydride type curing agent, active ester and free radical initiator, or a combination of at least two selected therefrom.

Preferably, the halogen-free flame retardant resin composition further comprises a filler.

Preferably, the filler is anyone selected from the group consisting of silica, alumina, titania, barium titanate, strontium titanate, magnesium titanate, calcium titanate, barium strontium titanate, lead titanate and glass powder, or a combination of at least two selected therefrom.

Preferably, the silica is selected from fused amorphous silica and/or crystalline silica, preferably fused amorphous silica.

Preferably, the titanium dioxide is selected from rutile-type titanium dioxide and/or anatase-type titanium dioxide, preferably rutile-type titanium dioxide.

On the other side, the present invention provides a resin glue obtained by dissolving or dispersing the halogen-free flame retardant resin composition of the present invention in a solvent.

Preferably, the solvent is one selected from the group consisting of ketones, hydrocarbons, ethers, esters and aprotic solvents, or a combination of at least two selected therefrom, preferably acetone, methyl ethyl ketone, methyl isobutyl ketone, toluene, xylene, methanol, ethanol, primary alcohol, ethylene glycol monomethyl ether, propylene glycol monomethyl ether, propylene glycol methyl ether acetate, ethyl acetate, N,N-dimethylformamide and N,N-diethylformamide, or a mixture of at least two selected therefrom. Said solvent may be used separately or in combination. The amount of the solvent can be determined by those skilled in the art according to the viscosity of the resin used therein, so that the viscosity of the resin glue solution is moderate to facilitate curing, and the present invention is not limited thereto.

On the other side, the present invention provides a prepreg prepared by using the halogen-free flame retardant resin composition as stated in the first aspect. The alkyl polyol glycidyl ether resin composition of the present invention is adhered to a reinforcing material by impregnation and drying to form a prepreg.

In the present invention, the reinforcing material may be an inorganic or organic material. The inorganic material may be a woven fabric such as glass fiber, carbon fiber, boron fiber, metal, or a nonwoven fabric or paper. E-glass, Q-type cloth, NE cloth, D-type cloth, S-type cloth, high-silica cloth, and the like can be used for the glass fiber cloth or the nonwoven fabric. Woven fabric or nonwoven fabric or paper is made of an organic material such as polyester, polyamine, polyacrylic acid, polyimide, aramid, polytetrafluoroethylene, syndiotactic polystyrene, etc. However, the reinforcing material is not limited thereto. Other reinforcing materials which can be used for reinforcing resins can also be used for the present invention.

On the other side, the present invention provides a metal-clad laminate comprising one or at least two superimposed prepregs and metal foil located on one or both sides of the prepreg.

As compared to the prior art, the present invention has the following beneficial effects.

(1) The surface modification of cyclotriphosphazene flame retardants containing hydroxyl and aryl phosphorus oxygen structure by siloxane, and the introduction of the groups that can cross-react with resin systems can effectively improve the compatibility of cyclotriphosphazene flame retardants containing aryl phosphorus oxygen structure in thermosetting resins, reduce precipitation, and effectively play a role of the flame retardant effect of the flame retardant in the resin cured product.

(2) The long alkyl chain of siloxane introduced to the surface of the flame retardant onto which aromatic groups are accumulated can effectively improve the flexibility of the cured product and improve the stability of the resin cured product in processing.

(3) Silicon element is a kind of good organic flame-retarding element, which can improve the efficiency of the flame retardant when built in the molecular structure of the flame retardant of the present invention. In order to meet the flame retardant requirement of UL 94V-0 level, the demand for the agent is reduced.

(4) In the present invention, three kinds of structures of siloxane, aryl phosphorus oxygen structure and cyclotriphosphazene are built in one formula so that the resultant flame retardant combines the advantages of three kinds of structures and improves the compatibility between the flame retardant and the resin, greatly improving the flame retardant property and stability of the resin cured product.

EMBODIMENTS

The technical solution of the present invention is further explained below by specific embodiments. Those skilled in the art should know that the examples are only to assist in understanding the present invention, and should not be construed as limiting the present invention.

Example 1

(1) The cyclotriphosphazene compound DOPO-HAP containing DOPO having the following structure was synthesized according to the document (Qian, L., et al. (2011). "The non-halogen flame retardant epoxy resin based on a novel compound with phosphaphenanthrene and cyclotriphosphazene double functional groups." *Polymer Degradation and Stability* 96(6): 1118-1124)

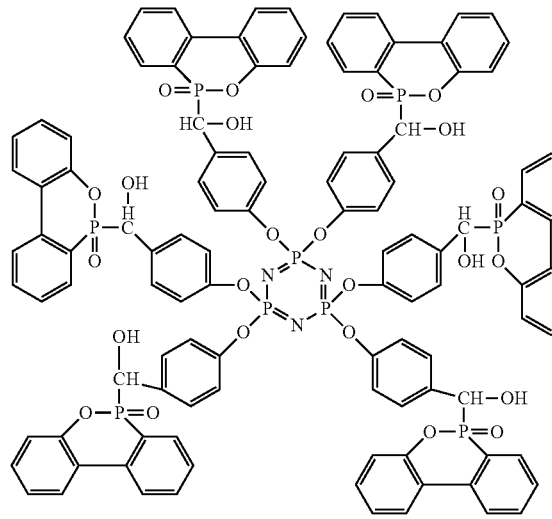

According to the reference document above, the synthetic method is stated as follows.

Into a four-necked flask equipped with a thermometer, a nitrogen inlet tube, a magnet, and a reflux condenser were added 34.8 g of cyclotriphosphazene, 85.6 g of p-hydroxybenzaldehyde and 75 g of sodium carbonate. Then 600 mL of tetrahydrofuran was added, and nitrogen was fed to heat to 60° C. and react for 28 h while stirring. After cooling, the by-product salt and residual sodium carbonate were filtered to remove. The filtrate was subject to rotary evaporation to remove the solvent dioxane, to obtain a milky white solid. The aforesaid solid was dissolved in 500 mL of 5% $Na_2CO_3$ solution and washed to remove excess p-hydroxybenzaldehyde. The solid was washed several times with pure water until the filtrate became neutral. The solid was dried in an oven at 80° C. for 8 h to obtain a white powder crude product with a yield of about 94%. The aforesaid crude product was recrystallized by ethyl acetate to give a white crystal. The solid was vacuum-dried at 50° C. for 6 h with a yield of 88.6 wt %. Into a four-necked flask equipped with a thermometer, a nitrogen inlet tube, a magnet, and a reflux condenser were added 89.1 g of DOPO, 100 mL of N,N-dimethylformamide, heated to 120° C. and stirred until completely being dissolved. Nitrogen was fed, and 38.2 g of hexa-(4-aldehyde-phenoxy)-cyclotriphosphazene was added to continue the stirring at 140° C. and react for 10 h. After cooling, the reaction solution was slowly added dropwise to ice water. A white solid was precipitated, filtered, and ultrasonically washed with ice water three times and filtered. The filter cake was washed with toluene and ethanol three times, and then placed under vacuum conditions at 90° C. for 10 h, to obtain the white product DOPO-HAP.

(2) Cyclotriphosphazene (DOPO-HAP) having hydroxyl and aryl phosphorus oxygen structure in step (1) was dissolved in a DMF solvent, and nitrogen was introduced thereinto. Siloxane monomer was added in a mass ratio of DOPO-HAP:KBM403 (Nippon Shin-Etsu Chemical Co., Ltd) of 2:1. A catalyst zinc isooctanoate in an amount of 0.5% by mass of the siloxane monomer was added. Deionized water was added in an amount of 0.7 time of the molar number of siloxane-$OCH_3$, to react at 90° C. for 4 h, and then to heat to 110° C. and to react for 3 h. After cooling, the viscous reaction product was introduced into ice-acetone to precipitate a white soft solid DHS-1 having the structure as shown in the following formula:

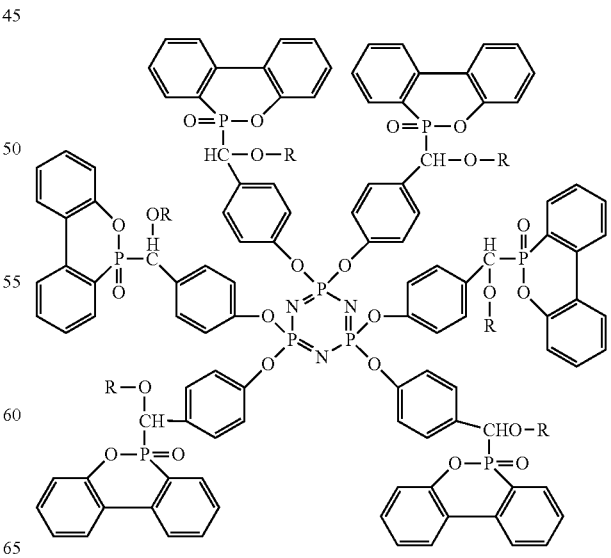

wherein six Rs are independently

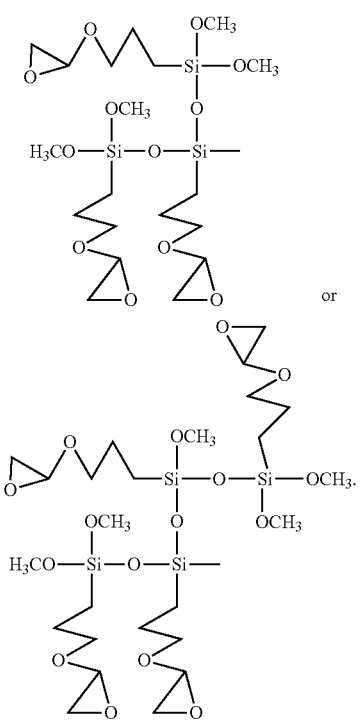

or

The epoxy value of the solid product was determined by the acetone-hydrochloride method to be 0.11-0.14; the molecular weight Mn thereof was 3050-3450 (DMF). The infrared spectrum of DHS-1 (shortened as FT-IR, KBr) was P=N (1157, 1176, 1216 cm$^{-1}$), P—O-Ph (963, 743 cm$^{-1}$), P=O (1193 cm$^{-1}$), —CH$_3$, CH$_2$ (2940 cm$^{-1}$), —Si—O— (1120 cm$^{-1}$),

(912 cm$^{-1}$). The nuclear magnetic resonance spectrum (NMR, deuterated DMSO solvent in ppm, the same below) of DHS-1 was that $^1$H-NMR, 7.49 (Ar—H), 7.58 (Ar—H), 7.78 (Ar—H), 4.0-4.1 (CH), 3.1-3.2 (CH$_2$), 3.50-3.54 (—OCH$_3$), 3.14, 2.79 were respectively the absorption peaks of CH, CH$_2$ hydrogen protons on the epoxy groups; $^{31}$P-NMR:33.9 was DOPO phosphorus atom absorption peak; 7.98 was the phosphorus atom absorption peak in cyclotriphosphazene; $^{29}$Si-NMR:–22.3 ppm.

50 parts by weight of Hexion bisphenol A type novolac epoxy resin EP627, 15.5 parts by weight of a curing agent DDS (4,4-diaminodiphenylsulfone) and 12 parts by weight of the flame retardant DHS-1 prepared as above were dissolved in DMF. 22.5 parts by weight of fumed silica was added, homogeneously dispersed to prepare corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Example 2

(1) The cyclotriphosphazene compound DOPO-HAP containing DOPO was prepared according to the same preparation process as stated in step (1) of Example 1.

(2) The cyclotriphosphazene DOPO-HAP containing DOPO prepared in step (1) was dissolved in a DMF solvent, and nitrogen was added thereto. Siloxane monomer was added in a mass ratio of DOPO-HAP:KBM403 (Nippon Shin-Etsu Chemical Co., Ltd.) of 4:1, and a catalyst dibutyltin dilaurate was added in an amount of 0.3% by mass of the siloxane monomer. Deionized water was added in an amount equal to the molar number of siloxane-OCH$_3$, and the reaction was carried out at 90° C. for 3 h. Then, the reaction mixture was heated to 110° C. for 6 h. After cooling, the viscous reaction product was introduced into ice-acetone to precipitate a white soft solid DHS-2 having the structure as shown in the following formula:

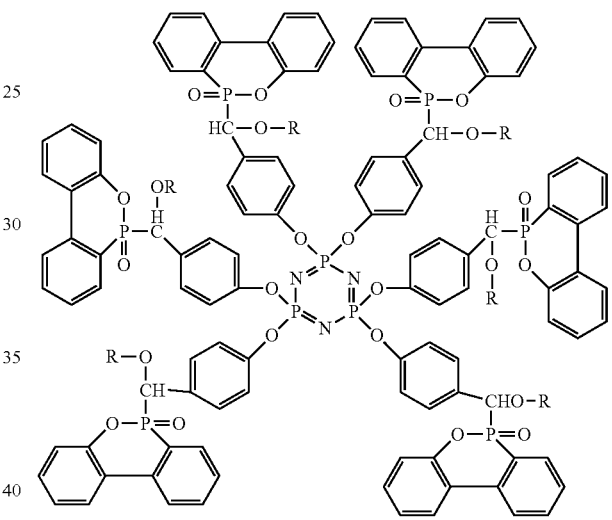

wherein six Rs are independently

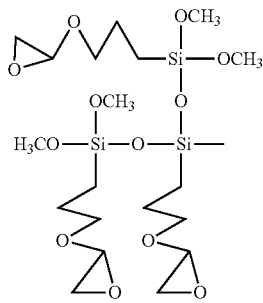 [SMILES: CO[Si](CCCOC1CO1)(OC)O[Si](C)(CCCOC1CO1)O[Si](CCCOC1CO1)(OC)OC]

or H (not all H).

The epoxy value of the solid product was determined by the acetone-hydrochloride method to be 0.06-0.09; the molecular weight Mn thereof was 2450-2850 (DMF). The infrared spectrum of DHS-2 (shortened as FT-IR, KBr) was P=N (1157, 1176, 1216 cm$^{-1}$), P—O-Ph (963, 743 cm$^{-1}$), P=O (1193 cm$^{-1}$), —CH$_3$, CH$_2$ (2940 cm$^{-1}$), —Si—O— (1120 cm$^{-1}$), (912 cm$^{-1}$). The nuclear magnetic resonance spectrum (NMR, deuterated DMSO solvent in ppm, the same below) of DHS-2 was that $^1$H-NMR, 7.49 (Ar—H), 7.58 (Ar—H), 7.78 (Ar—H), 4.0-4.1 (CH), 3.1-3.2 (CH$_2$), 3.50-3.54 (—OCH$_3$), 3.14, 2.79 were respectively the absorption peaks of CH, CH$_2$ hydrogen protons on the epoxy groups; $^{31}$P-NMR:33.9 was DOPO phosphorus atom absorption peak; 7.98 was the phosphorus atom absorption peak in cyclotriphosphazene; $^{29}$Si-NMR:-22.3 ppm. 

30 parts by weight of Hexion bisphenol A type novolac epoxy resin EP627, 36 parts by weight of DOW Chemical Bisphenol A epoxy resin EP828, 8.5 parts by weight of a dicyandiamide curing agent DICY, 16.5 parts by weight of the flame retardant DHS-2 were dissolved in DMF. 9 parts by weight of barium titanate was added, homogeneously dispersed to prepare corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Example 3

(1) The cyclotriphosphazene compound DOPO-HAP containing DOPO was prepared according to the same preparation process as stated in step (1) of Example 1.

(2) The cyclotriphosphazene DOPO-HAP containing DOPO prepared in step (1) was dissolved in a DMF solvent, and nitrogen was added thereto. Siloxane monomer was added in a mass ratio of DOPO-HAP:KBM903 (Nippon Shin-Etsu Chemical Co., Ltd.) of 3:1, and a catalyst cobalt acetylacetonate was added in an amount of 0.1% by mass of the siloxane monomer. Deionized water in an amount of 1.3 times of the molar number of siloxane-OCH$_3$ was added, and the reaction was carried out at 75° C. for 7 h. Then, the reaction mixture was heated to 100° C. for 2 h. After cooling, the viscous reaction product was introduced into ice-acetone to precipitate a white soft solid DHS-3 having the structure as shown in the following formula:

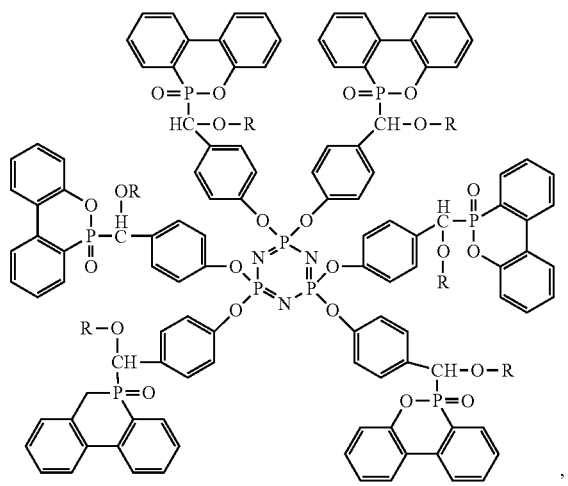

wherein six Rs are independently

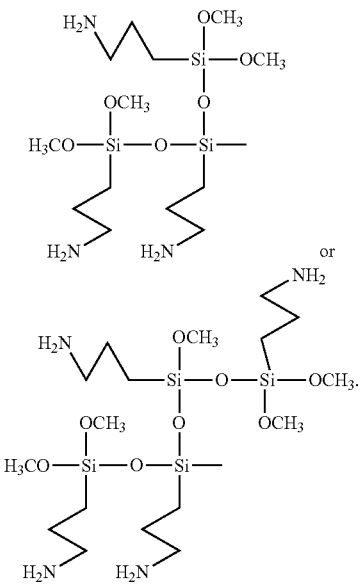

The amine value of the solid product DHS-3 was determined by the perchloric acid-acetic acid method to be 0.011-0.014; the molecular weight Mn thereof was 2800-3300 (DMF). The FT-IR of DHS-3 (KBr) was P=N (1152, 1176, 1213 cm$^{-1}$), P—O-Ph (961, 745 cm$^{-1}$), P=O (1198 cm$^{-1}$), —NH$_2$ (3226, 3325 cm$^{-1}$), —OH (3427 cm$^{-1}$), —CH$_3$, CH$_2$ (2938, 2865 cm$^{-1}$), —Si—O— (1126 cm$^{-1}$). The NMR of DHS-3 was that $^1$H-NMR, 9.82 (—OH, weak), 7.49 (Ar—H), 7.58 (Ar—H), 7.78 (Ar—H), 4.0-4.1 (CH$_3$), 2.62-2.96 (CH$_2$), 1.76-1.93 (CH$_2$), 1.26-1.46 (CH$_2$), 3.35-3.54 (NH$_2$). $^{31}$P-NMR:31.89 was DOPO phosphorus atom absorption peak; 7.56 was the phosphorus atom absorption peak in cyclotriphosphazene; $^{29}$Si-NMR:-26.8 ppm.

55 parts by weight of DIC epoxy resin 7200H from Japanese Ink, 21.5 parts by weight of an anhydride curing agent EF60 from Sodomar, 1.0 part by weight of a curing agent DDS and 16.5 parts by weight of the flame retardant DHS-3 were dissolved in DMF. 6 parts by weight of fumed silica was added to produce corresponding resin glue, and to coat the glue onto 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Example 4

(1) Phenol and p-hydroxybenzaldehyde in a molar ratio of 1.0:5.2 (totaling 0.682 mol) were added to tetrahydrofuran solution. Nitrogen was introduced, and triethylamine was added. The mixture was stirred for 2 hours at room temperature until no white smoke was generated in the reaction flask. 0.1 mol hexachlorocyclotriphosphazene was dissolved in dry tetrahydrofuran solution, and then dropped into the reaction flask in 60 min. Then after refluxing for 28 hours, the solvent was removed after reaction, to recrystallize and to obtain the product (1,2,3,4,5-penta-p-aldehydephenoxy-6-phenoxy-cyclotriphosphazene) having the following structure:

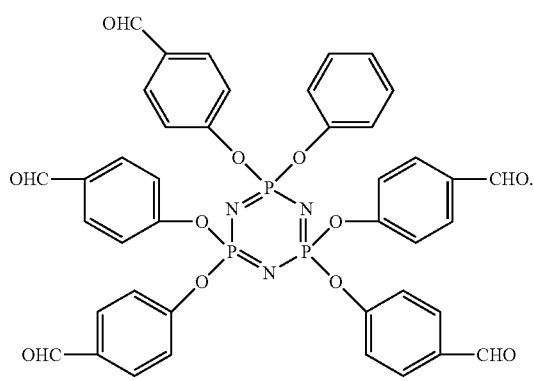 [SMILES: O=Cc1ccc(OP2(Oc3ccccc3)=NP(Oc3ccc(C=O)cc3)(Oc3ccc(C=O)cc3)=NP(Oc3ccc(C=O)cc3)(Oc3ccc(C=O)cc3)=N2)cc1]

The structural characterization data of this product are shown below, FT-IR (KBr): CHO (2739 cm$^{-1}$), C=O (1708 cm$^{-1}$), P=N (1153, 1171, 1225 cm$^{-1}$); $^1$H-NMR:9.93 (s, —CHO), 7.92-7.82 (d, protons on benzene ring), 7.34-7.18 (d, protons on benzene ring); ESI molecular weight: [M+1]$^+$ being 834.25, elemental analysis: C, 59.18, H, 3.76, N, 5.21, O, 21.29.

(2) 200 mL of dioxane was added into the reactor, and 0.21 mol of diphenylphosphine oxide (Guangzhou Shengbao Chemical Co., Ltd., the same below) was added. After complete dissolving 0.2 mol of 1,2,3,4,5-penta-p-aldehydephenoxy-6-phenoxy-cyclotriphosphazene obtained in step (1) was added. Nitrogen was fed for protection to react at 100° C. under reflux for 16 hours. Dioxane was removed by distillation under reduced pressure, to obtain a white solid product having the following chemical structure. The product was washed with ethyl acetate and vacuum-dried in at 80° C. to constant weight to give a white powdery solid (TPHC) having a yield of 95.5% and the following structure below.

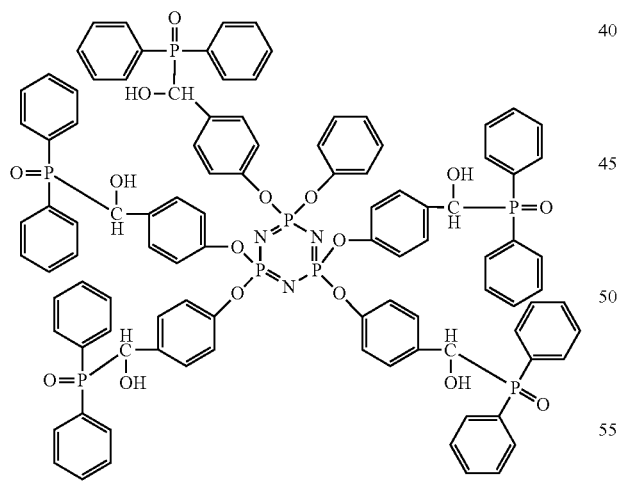

The structural characterization data are as follows: FT-IR (KBr): OH (3395 cm$^{-1}$), P=O (1256 cm$^{-1}$), P—O-Ph (942, 751 cm$^{-1}$), P=N (1202, 1193, 1161 cm$^{-1}$); $^1$H-NMR:7.51-8.21 (m, protons on benzene ring), 6.47-7.36 (m, protons on benzene ring), 6.54 and 6.83 (d, —OH), 5.18 and 5.39 (d, —CH—); $^{31}$P-NMR:8.78 (phosphorus atom on cyclotriphosphazene) 和 □ 31.19 (phosphorus atom on diphenylphosphine oxide). Elemental analysis: C: 62.52; (cal 63.43), H: 4.05; (cal 3.92) and N: 1.87; (cal 1.95).

(3) TPHC having the aforesaid structure was dissolved in a DMF solvent, and nitrogen was introduced thereinto. Siloxane monomer was added in a mass ratio of TPHC:KBM403 (Nippon Shin-Etsu Chemical Co., Ltd) of 4:1. A catalyst copper acetylacetonate in an amount of 0.8% by mass of the siloxane monomer was added. Deionized water was added in an amount equal to the molar number of siloxane-OCH$_3$, to react at 90° C. for 3 h, and then to heat to 110° C. and to react for 6 h. After cooling, the viscous reaction product was introduced into ice-acetone to precipitate a white soft solid DHS-4 having the structure as shown in the following formula:

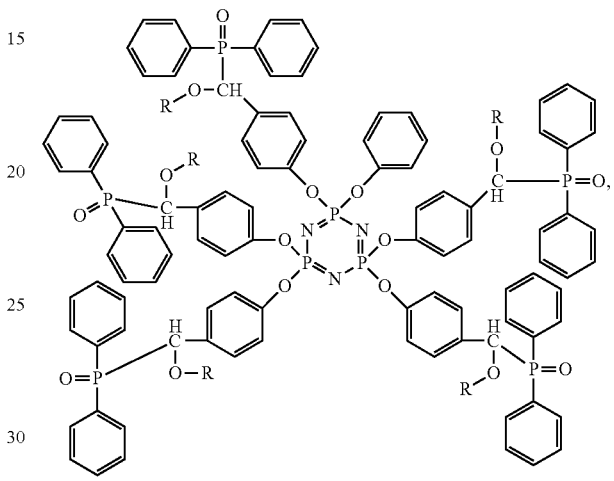

wherein six Rs are independently

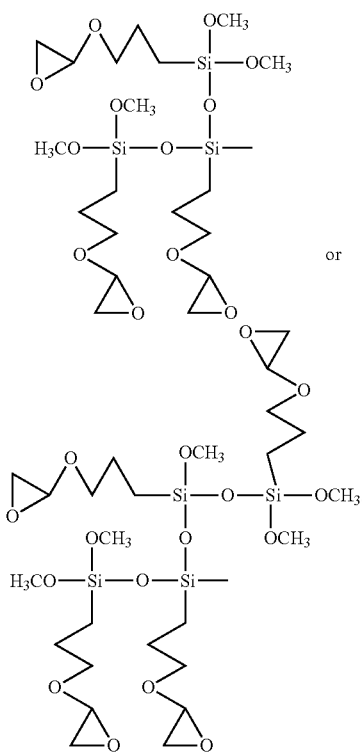

The epoxy value of the solid product DHS-4 was determined by the acetone-hydrochloride method to be 0.05-0.09;

the molecular weight Mn thereof was 2550-2800 (DMF). The FT-IR of DHS-4 (KBr) was OH (3395 cm$^{-1}$), P=O (1261 cm$^{-1}$), P—O-Ph (939, 754 cm$^{-1}$), P=N (1209, 1195, 1164 cm$^{-1}$), —CH$_3$, CH$_2$ (2939, 2847 cm$^{-1}$), —Si—O— (1126 cm$^{-1}$),

(925 cm$^{-1}$). The NMR of DHS-4 was that $^1$H-NMR, 9.78 (—OH, weak), 7.51 (Ar—H), 7.58 (Ar—H), 7.78 (Ar—H), 4.1-4.3 (CH), 3.0-3.2 (CH$_2$), 3.50-3.54 (—OCH$_3$), 3.14, 2.79 were respectively the absorption peaks of CH, CH$_2$ hydrogen protons on the epoxy groups. $^{31}$P-NMR:33.9 was DOPO phosphorus atom absorption peak; 7.98 was the phosphorus atom absorption peak in cyclotriphosphazene; $^{29}$Si-NMR:−23.4 ppm.

48 parts by weight of the diamine-type benzoxazine D125 from Sichuan Eastwood Science & Technology Co., 18.5 parts by weight of DIC epoxy resin 7200H from Japanese Ink, 18.5 parts by weight of the flame retardant DHS-4 were dissolved in DMF. 15 parts by weight of aluminium oxide were added, homogeneously dispersed to prepare corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Example 5

(1) Phenol and o-hydroxybenzaldehyde in a molar ratio of 1.0:1.2 (totaling 0.682 mol) were added to tetrahydrofuran solution. Nitrogen was introduced, and triethylamine was added. The mixture was stirred for 2 hours at room temperature until no white smoke was generated in the reaction flask. 0.1 mol hexachlorocyclotriphosphazene was dissolved in dry tetrahydrofuran solution, and then dropped into the reaction flask in 60 min. Then after refluxing for 25 hours, the solvent was removed after reaction, to recrystallize and to obtain 1,3,5-tri-o-aldehydephenoxy-6-phenoxy-cyclotriphosphazene having the following structure:

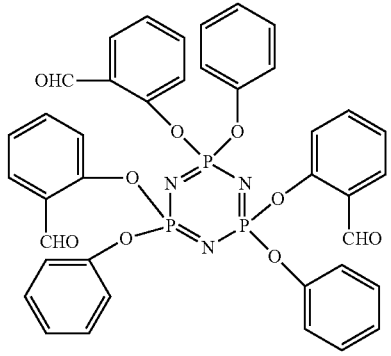 [SMILES: O=Cc1ccccc1OP1(Oc2ccccc2)=NP(Oc2ccccc2)(Oc2ccccc2C=O)=NP(Oc2ccccc2)(Oc2ccccc2C=O)=N1]

ESI molecular weight: [M+Na]$^+$ being 800.25, elemental analysis: C, 60.18, H, 3.76, N, 5.21, O, 18.29.

(2) According to the reference document [A. Schäfer, S Seibold, W Lohstroh, O Walter, M Döring. Synthesis and properties of flame-retardant epoxy resins based on DOPO and one of its analog DPPO. Journal of Applied Polymer Science, 2007, 105(2):685-696], DPPO was synthesized by the following method. 59.4 g of p-dimethyldiphenyl ether, 105 ml of phosphorus trichloride and 39.6 g of aluminum trichloride were fed into a 1 L reaction flask with a condenser tube at room temperature. Nitrogen was introduced into the reaction flask, and slowly heated to 85° C. for 24 h. After cooling, the reaction mixture was poured into ice water and filtered. The crude product was washed successively with 1.0 mol/L hydrochloric acid, saturated sodium carbonate and deionized water. The crude product was crystallized from benzene and vacuum-dried at 120° C. for 24 hours to give the target product DPPO.

200 mL of dioxane was added into the reactor, and 0.42 mol of DPPO was added. After complete dissolving 0.1 mol of 1,3,5-tri-o-aldehydephenoxy-6-phenoxy-cyclotriphosphazene obtained in step (1) was added. Nitrogen was fed for protection to react 100° C. under reflux for 21 hours. Dioxane was removed by distillation under reduced pressure, to obtain a white solid product having the following chemical structure. The product was washed with ethyl acetate and vacuum-dried at 80° C. to constant weight to give a white powdery solid (TDHC) having a yield of 89.5% and the following structure below:

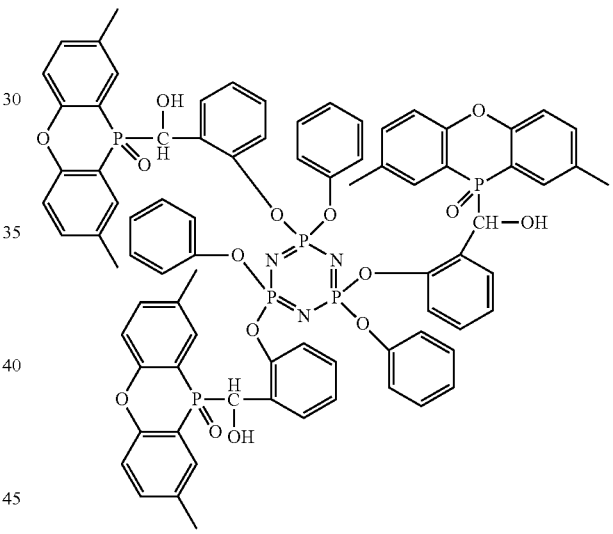

$^{31}$P-NMR (d$_6$-DMSO, ppm): 8.98 (phosphorus on cyclotriphosphazene) and 34.96 (phosphorus atom on DPPO). Elemental analysis: C: 62.52; (cal 63.43), H: 4.05; (cal 3.92) and N: 1.87; (cal 1.95).

(3) The cyclotriphosphazene compound (TDHC) in step (2) was dissolved in a DMF solvent, and nitrogen was introduced thereinto. Siloxane monomer 3-ureidopropyltriethoxysilane was added in a mass ratio of TDHC:3-ureidopropyltriethoxysilane (Nanjing QX Chemical Co., Ltd) of 1:1. A catalyst cobalt isooctanoate in an amount of 0.4% by mass of the siloxane monomer was added. Deionized water was added in an amount equal to the molar number of siloxane-OCH$_3$, to react at 75° C. for 6 h, and then to heat to 105° C. and to react for 6 h. After cooling, the viscous reaction product was introduced into ice-acetone to precipitate a white soft solid DHS-5 having the structure as shown in the following formula:

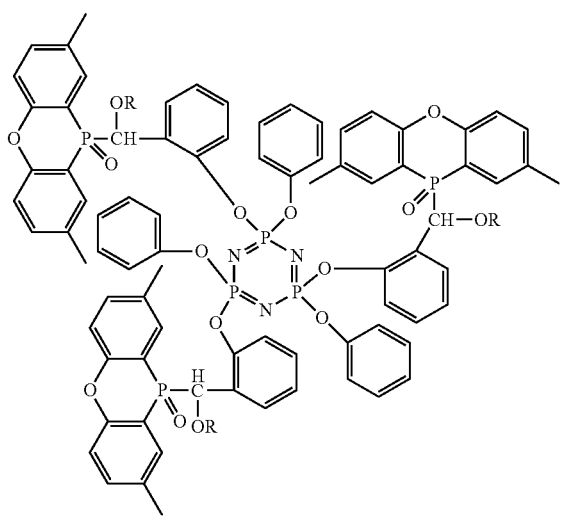 [SMILES: Cc1ccc2c(c1)P(=O)(C(O)c1ccccc1OP1(Oc3ccccc3)=NP(Oc3ccccc3)(Oc3ccccc3C(O)P3(=O)c4cc(C)ccc4Oc4ccc(C)cc43)=NP(Oc3ccccc3)(Oc3ccccc3C(O)P3(=O)c4cc(C)ccc4Oc4ccc(C)cc43)=N1)c1cc(C)ccc1O2]

wherein R is

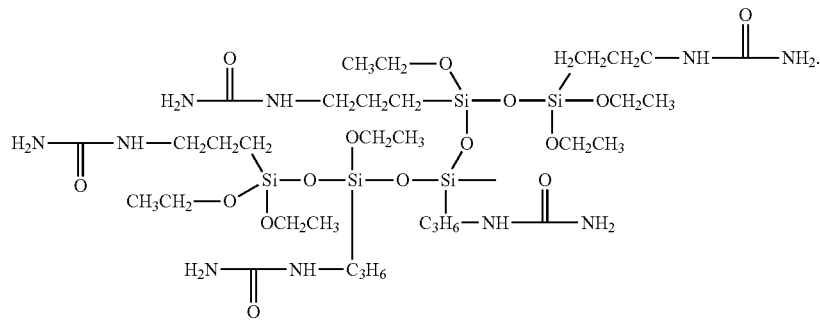

The amine value of the solid product DHS-5 was determined by the perchloric acid-acetic acid method to be 0.012-0.017; the molecular weight Mn thereof was 2800-3300 (DMF). The FT-IR of DHS-5 (KBr) was C=O (1698, 1745 cm$^{-1}$) P=O (1298 cm$^{-1}$), P—O-Ph (951, 786 cm$^{-1}$), P=N (1211, 1189, 1164 cm$^{-1}$), —CH$_3$, CH$_2$ (2956, 2865 cm$^{-1}$), —Si—O— (1190 cm$^{-1}$),

(925 cm$^{-1}$).

The NMR of DHS-5 was that $^1$H-NMR, 7.43 (Ar—H), 7.52 (Ar—H), 7.82 (Ar—H), 3.50-3.54 (—OCH$_3$), 2.62-2.96 (CH$_2$), 1.76-1.93 (CH$_2$), 1.26-1.46 (CH$_2$), 4.35-4.6 (NH), 3.35-3.54 (NH$_2$) 3. $^{31}$P-NMR:35. 9 was DOPO phosphorus atom absorption peak; 7.52 was the phosphorus atom absorption peak in cyclotriphosphazene; $^{29}$Si-NMR:−28.6 ppm.

50 parts by weight of Hexion bisphenol A type novolac epoxy resin EP627, 8.5 parts by weight of a curing agent bisphenol A type benzoxazine 8290 from Taiwan Huntsman, 7 parts by weight of DDS, and 21.5 parts by weight of the flame retardant DHS-5 were dissolved in DMF. 13 parts by weight of fumed silica was added, homogeneously dispersed to prepare corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Example 6

(1) Phenol and p-hydroxybenzaldehyde in a molar ratio of 3.0:3.2 (totaling 0.682 mol) were added to tetrahydrofuran solution. Nitrogen was introduced, and anhydrous sodium carbonate was added. The mixture was stirred for 3 hours at room temperature. 0.1 mol hexachlorocyclotriphosphazene was dissolved in dry tetrahydrofuran solution, and then dropped into the reaction flask in 60 min. Then after refluxing for 20 hours, the solvent was removed after reaction, to recrystallize and to obtain 1,3,5-penta-p-aldehydephenoxy-2,4,6-triphenoxy-cyclotriphosphazene having the following structure:

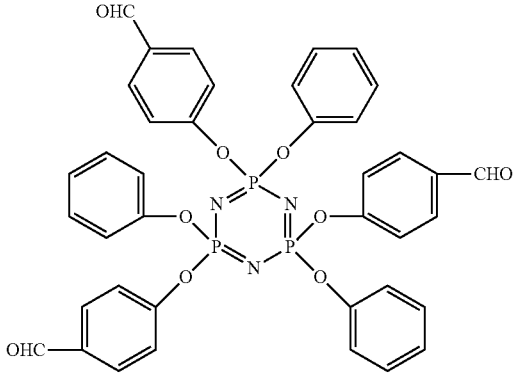 [SMILES: O=Cc1ccc(OP2(Oc3ccccc3)=NP(Oc3ccccc3)(Oc3ccc(C=O)cc3)=NP(Oc3ccccc3)(Oc3ccc(C=O)cc3)=N2)cc1]

ESI molecular weight: [M+1]$^+$ being 834.25, elemental analysis: C, 59.18, H, 3.76, N, 5.21, O, 21.29.

(2) According to the reference document (Xia, X., et al. (2006). "Synthesis of Novel Phosphorous-Containing Biphenol,2-(5,5-Dimethyl-4-phenyl-2-oxy-1,3,2-dioxaphosphorin-6-yl)-1,4-benzenediol and Its Application as Flame-Retardant In Epoxy Resin." *Journal of Applied Polymer Science* 102: 3842-3847), 1,2-dioxaphosphorinane naphthol was synthesized by the following method. At room temperature, 1,8-dihydroxynaphthalene, phosphorus trichloride, tetrahydrofuran and aluminum trichloride were added to a reaction flask with a condenser tube and a gas collector at a stoichiometric ratio. Nitrogen was fed therein, and the temperature was slowly raised to 65° C. for 12 hours. The solvent was removed on a rotary evaporator, and a mixed solvent of $H_2O$ and ethanol was used to recrystallize to give the desired product.

200 mL of dioxane was added into the reactor, and 0.21 mol of 1,2-dioxaphosphorinane naphthol was added. After complete dissolving 0.2 mol of 1,3,5-penta-p-aldehydephenoxy-2,4,6-triphenoxy-cyclotriphosphazene obtained in step (1) was added. Nitrogen was fed for protection to react 100° C. under reflux for 20 hours. Dioxane was removed by distillation under reduced pressure, to obtain a white solid product having the following chemical structure. The product was washed with a mixed solvent of ethyl acetate/acetone and vacuum-dried at 80° C. to constant weight to give a white powdery solid (TNHC) having a yield of 95.5% and the following structure below:

zene ring), 6.47-7.36 (m, protons on benzene ring), 6.29 and 6.51 (d, —OH), 5.28 and 5.43 (d, —CH—, 6H); $^{31}$P-NMR (d$_6$-DMSO, ppm): 8.78 (phosphorus atom on cyclotriphosphazene) and 29.60 (phosphaphenanthrene phosphorus atom). Elemental analysis: C: 62.52; (cal 63.43), H: 4.05; (cal 3.92) and N: 1.87; (cal 1.95).

(3) Phosphorus-containing cyclotriphosphazene containing hydroxyl (TNHC) in step (2) was dissolved in a DMF solvent, and nitrogen was introduced thereinto. Siloxane monomer was added in a mass ratio of TNHC:KBM403 (Nippon Shin-Etsu Chemical Co., Ltd) of 1:1. A catalyst iron isooctanoate in an amount of 0.5% by mass of the siloxane monomer was added. Deionized water was added in an amount equal to the molar number of siloxane-OCH$_3$, to react at 80° C. for 5 h, and then to heat to 120° C. and to react for 6 h. After cooling, the viscous reaction product was

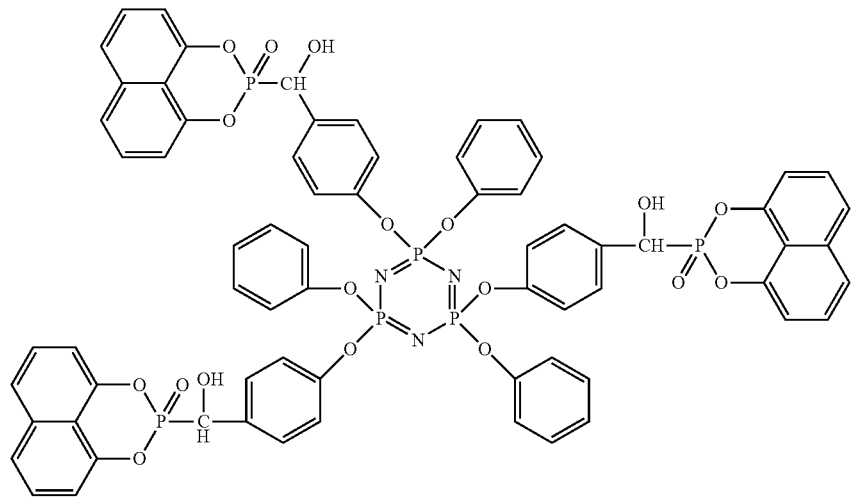 [SMILES: O=P1(C(O)c2ccc(OP3(Oc4ccccc4)=NP(Oc4ccccc4)(Oc4ccc(C(O)P5(=O)Oc6cccc7cccc(c67)O5)cc4)=NP(Oc4ccccc4)(Oc4ccc(C(O)P5(=O)Oc6cccc7cccc(c67)O5)cc4)=N3)cc2)Oc2cccc3cccc(c23)O1]

FT-IR (KBr): OH (3416 cm$^{-1}$), P═O (1256 cm$^{-1}$), P—O-Ph (945 and 764 cm$^{-1}$), P═N (1211, 1196, 1151 cm$^{-1}$); $^1$H-NMR (d$_6$-DMSO, ppm): 7.61-8.21 (m, protons on benintroduced into ice-acetone to precipitate a white soft solid DHS-6 having the structure as shown in the following formula:

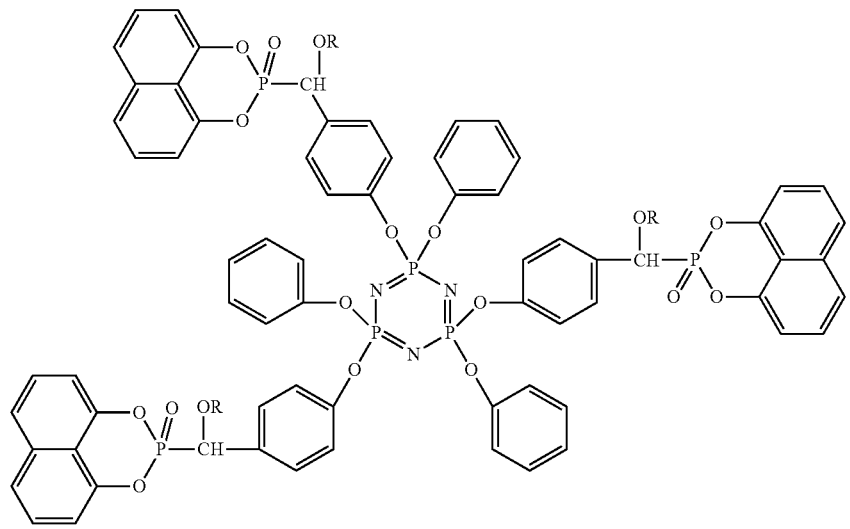

wherein three Rs are independently

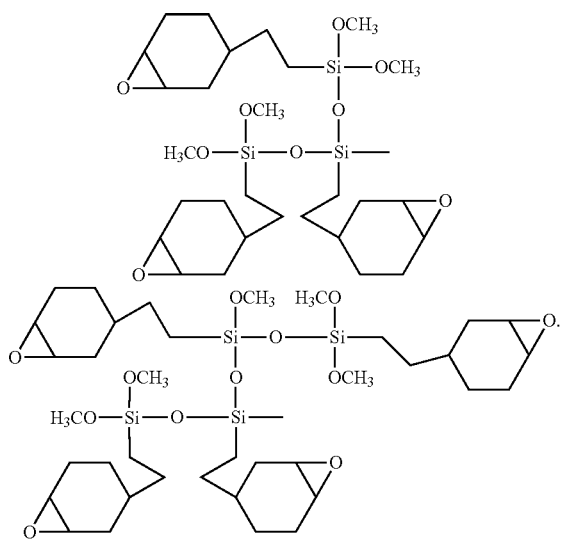

The epoxy value of the solid product DHS-6 was determined by the acetone-hydrochloride method to be 0.05-0.09; the molecular weight Mn thereof was 2550-2800 (DMF). The FT-IR of DHS-6 (KBr) was P=O (1256 cm$^{-1}$), P—O-Ph (945, 764 cm$^{-1}$), P=N (1211, 1196, 1151 cm$^{-1}$), —CH$_3$, CH$_2$ (2956, 2865 cm$^{-1}$), —Si—O— (1100 cm$^{-1}$),

(931 cm$^{-1}$). The NMR of DHS-6 was that $^1$H-NMR, ppm, 7.61-8.21 (m, hydrogen on benzene ring), 6.47-7.36 (m, hydrogen on benzene ring), 6.29 and 6.51 (d, —OH), 5.28 and 5.43 (d, —CH—, 6H), 4.0-4.1 (CH), 3.1-3.2 (CH$_2$), 3.50-3.54 (—OCH$_3$), 3.14, 2.79 were respectively the absorption peaks of CH, CH$_2$ hydrogen protons on the epoxy groups. $^{31}$P-NMR:35.9 was DOPO phosphorus atom absorption peak; 7.52 was the phosphorus atom absorption peak in cyclotriphosphazene; $^{29}$Si-NMR:−28.6 ppm.

50 parts by weight of Hexion bisphenol A type novolac epoxy resin EP627, 15.5 parts by weight of a curing agent DDS, and 22 parts by weight of the flame retardant DHS-6 were dissolved in DMF. 12.5 parts by weight of fumed silica was added, homogeneously dispersed to prepare corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Comparison Example 1

50 parts by weight of Hexion bisphenol A type novolac epoxy resin EP627 and 15.5 parts by weight of a curing agent DDS were dissolved in DMF. 34.5 parts by weight of fused silica was added to produce corresponding glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Comparison Example 2

50 parts by weight of Hexion bisphenol A type novolac epoxy resin EP627, 15.5 parts by weight of a curing agent DDS and 12 parts by weight of a flame retardant DOPO-HAP were dissolved in DMF. 22.5 parts by weight of fused silica was added, homogeneously dispersed to produce corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Comparison Example 3

50 parts by weight of Hexion bisphenol A type novolac epoxy resin EP627, 15.5 parts by weight of a curing agent DDS and 18.5 parts by weight of a flame retardant DOPO-HAP were dissolved in DMF. 16 parts by weight of fused silica was added, homogeneously dispersed to produce corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

Comparison Example 4

50 parts by weight of Hexion bisphenol A type novolac epoxy resin EP627, 15.5 parts by weight of a curing agent DDS, 16.5 parts by weight of a cyclotriphosphazene flame retardant containing siloxane were dissolved in DMF. 18 parts by weight of fused silica was added, homogeneously dispersed to produce corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The cyclotriphosphazene flame retardant containing siloxane was the cyclotriphosphazene compound having the following structure disclosed in CN102250147A.

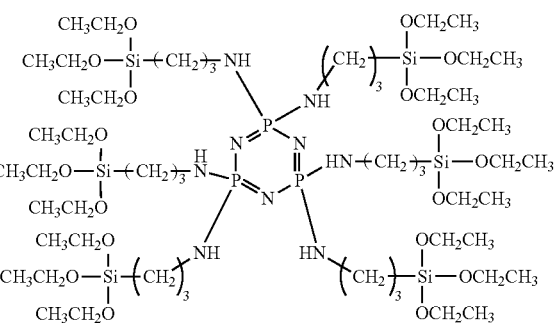

The main performances of the CCL prepared according to the Comparison Example are shown in Table 1.

Comparison Example 5

50 parts by weight of Hexion bisphenol A type novolac epoxy resin EP627, 15.5 parts by weight of a curing agent DDS, 8 parts by weight of a flame retardant DOPO-HAP and 8.5 parts by weight of cyclotriphosphazene flame retardant containing siloxane having the structure as shown in Comparison Example 4 disclosed in CN102250147A were dissolved in DMF. 18 parts by weight of fused silica was added, homogeneously dispersed to produce corresponding resin glue and to coat the glue on 7628 glass fiber cloth produced by TAIJIA GLASS FIBER CO., LTD. After drying solvent and preparing into prepregs, 8 sheets of prepregs were hot-pressed to produce a copper-clad laminate (CCL). The main performances of the board are shown in Table 1.

TABLE 1

| Flame retardant | Glass transition temperature (° C.) | 1% Weight-loss temperature (° C.) | Limit oxygen index LOI | UL 94 |
|---|---|---|---|---|
| Example 1 | 193 | 361 | 35.6% | V-0 |
| Example 2 | 201 | 375 | 36.7% | V-0 |
| Example 3 | 191 | 386 | 35.1% | V-0 |
| Example 4 | 199 | 395 | 34.6% | V-0 |
| Example 5 | 207 | 416 | 36.8% | V-0 |
| Example 6 | 194 | 396 | 34.8% | V-0 |
| Comparison Example 1 | 197 | 372 | 22.5% | Non-flame retardant |
| Comparison Example 2 | 193 | 326 | 30.1% | V-1 |
| Comparison Example 3 | 196 | 355 | 32.1% | V-1 |
| Comparison Example 4 | 163 | 306 | 33.2% | V-1 |
| Comparison Example 5 | 173 | 322 | 33.5% | V-1 |

As can be seen from Table 1, the copper-clad laminate prepared by using the siloxane-modified cyclotriphosphazene compound of the present invention as a flame retardant has a glass transition temperature of 190° C. or higher, 1% weight-loss temperature of 360° C. or above, limit oxygen index of greater than 34%, flame retardancy of the V-0 level, which shows that the combination of siloxane with phosphorus-containing compound and cyclotriphosphazene can improve the compatibility in the thermosetting resin, reduce precipitation, effectively play the flame-retardant effect, and improve the stability of the cured product.

In Comparison Example 1, the siloxane-modified cyclotriphosphazene compound of the present invention was not added as a flame retardant. As a result, the prepared copper-clad laminate does not have flame retardant property. In Comparison Example 2, DOPO-HAP was used as the flame retardant; UL 94 flame retardant grade can only reach V-1; and its 1% weight-loss temperature is significantly reduced, and the thermal stability gets worse. By comparing Example 1 with Comparison Example 2, it can be seen that the modification of DOPO-HAP with siloxanes not only improves the flame retardancy of the cured product, but also increases the 1% weight-loss temperature. On the basis of Comparison Example 2, Comparison Example 3 increased the amount of the DOPO-HAP flame retardant to 18.5 parts by weight. However, the cured product therein was still only able to meet the UL 94 V-1 flame retardancy requirement. By comparing Comparison Example 3 with Example 1, although the amount of the DOPO-HAP flame retardant is increased, the flame retardancy cannot be improved, which also shows that the silicone-modified cyclotriphosphazene compound flame retardant of the present invention has a higher flame retardant efficiency. Moreover, the introduction of the siloxane into the flame retardant structure of the present invention can reduce the amount of the flame retardant while improving the flame retardant effect.

In Comparison Example 4, the cyclotriphosphazene compound disclosed in CN102250147A, i.e. siloxane-modified cyclotriphosphazene compound, was used as a flame retardant. The flame retardancy of the prepared copper-clad laminate is only able to reach the V-1 level, and its glass transition temperature and 1% weight-loss temperature are significantly decreased. Comparison Example 5 discloses mixing the cyclotriphosphazene compound disclosed in CN102250147A with DOPO-HAP as a flame retardant to prepare a copper clad laminate. By comparing Comparison Examples 2 and 4, it can be seen that the flame retardancy, glass transition temperature and 1% weight-loss temperature thereof are all improved. However, as compared to the copper-clad laminate which is flame retardant-modified by the siloxane-modified cyclotriphosphazene flame retardant in the examples, the flame retardancy, glass transition temperature and 1% weight-loss temperature thereof are still relatively low. Thus, it is stated that, although simply mixing the siloxane-modified cyclotriphosphazene compound with the cyclotriphosphazene compound having aryl phosphorus oxygen structure can also make the system simultaneously contain siloxane, aryl phosphorus oxygen structure and cyclotriphosphazene structure, such simple mixing does not produce a significant increase in performances, indicating that the siloxane, aryl phosphorus oxygen structure and cyclotriphosphazene structures in the structural formula of the siloxane-modified cyclotriphosphazene compound of the present invention have a synergistic effect, and can significantly enhance the flame-retardant property and stability of copper-clad laminates.

The applicant declares that the present invention discloses a siloxane-modified cyclotriphosphazene halogen-free flame retardant, as well as the preparation process and use thereof, by using the aforesaid examples. However, the present invention is not limited to the above-described examples. That is to say, it does not mean that the present invention cannot be carried out unless the aforesaid examples are used. Those skilled in the art shall know clearly that any modification of the present invention, equivalent replacements of the ingredients of the product of the present invention, addition of auxiliary ingredients, selection of specific modes and the like all fall within the protection scope and disclosure scope of the present invention.

The invention claimed is:

1. A siloxane-modified cyclotriphosphazene halogen-free flame retardant, wherein the flame retardant has the structural formula as shown in Formula I:

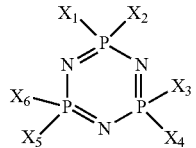

Formula I wherein the groups of $X_1$-$X_6$ are each independently selected from

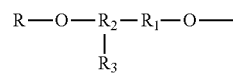

or —O—R', and at least two groups therein are

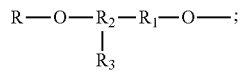

$R_1$ is a substituted or unsubstituted arylene; $R_2$ is selected from the group consisting of methenyl,

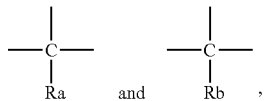

wherein $R_a$ is a substituted or unsubstituted C1-C5 alkyl group; $R_b$ is a substituted or unsubstituted aryl group; $R_3$ is a group containing aryl phosphorus oxygen structure; Rs in the groups of $X_1$-$X_6$ is independently selected from siloxane group or hydrogen, and Rs in the groups of $X_1$-$X_6$ are not hydrogen at the same time; R' is a substituted or unsubstituted aryl group.

2. The siloxane-modified cyclotriphosphazene halogen-free flame retardant according to claim 1, wherein $R_1$ is selected from the group consisting of

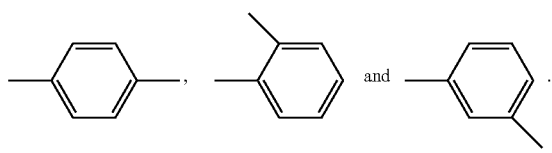

3. The siloxane-modified cyclotriphosphazene halogen-free flame retardant according to claim 1, wherein $R_3$ is selected from the group consisting of

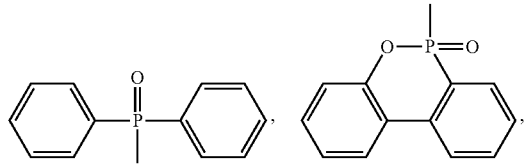

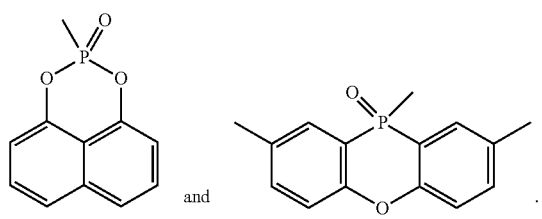

4. The siloxane-modified cyclotriphosphazene halogen-free flame retardant according to claim 1, wherein the siloxane group is selected from the group consisting of

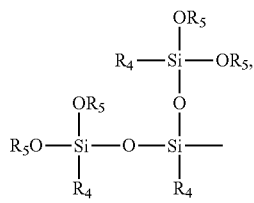

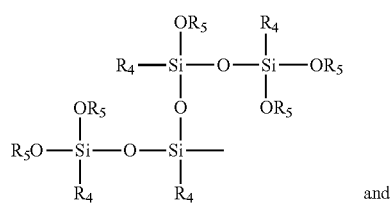

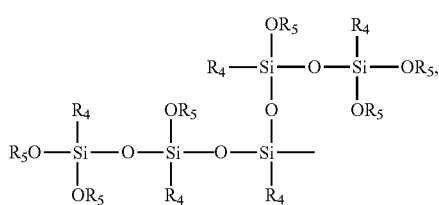

or a combination of at least two selected therefrom, wherein $R_4$ is selected from the group consisting of

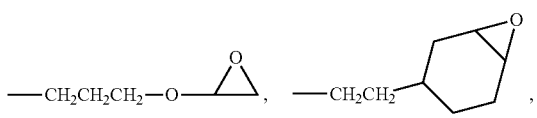

and —$CH_2CH_2CH_2NH$—$CH_2CH_2$—$NH_2$; $R_5$ is selected from C1-C5 alkyl groups.

5. The siloxane-modified cyclotriphosphazene halogen-free flame retardant according to claim 1, wherein R' is selected from the group consisting of substituted phenyl, unsubstituted phenyl, substituted naphthyl, unsubstituted naphthyl, substituted alkylphenyl, unsubstituted alkylphenyl, substituted cycloalkylphenyl, unsubstituted cycloalkylphenyl, substituted nitrophenyl, unsubstituted nitrophenyl, substituted nitrogen-containing heterocyclylphenyl, unsubstituted nitrogen-containing heterocyclylphenyl, substituted aryloxyphenyl, and unsubstituted aryloxyphenyl, or a combination of at least two selected therefrom.

6. The siloxane-modified cyclotriphosphazene halogen-free flame retardant according to claim 1, wherein the flame retardant is selected from the group of the compounds having the following formulae a-g, or a combination of at least two selected therefrom:

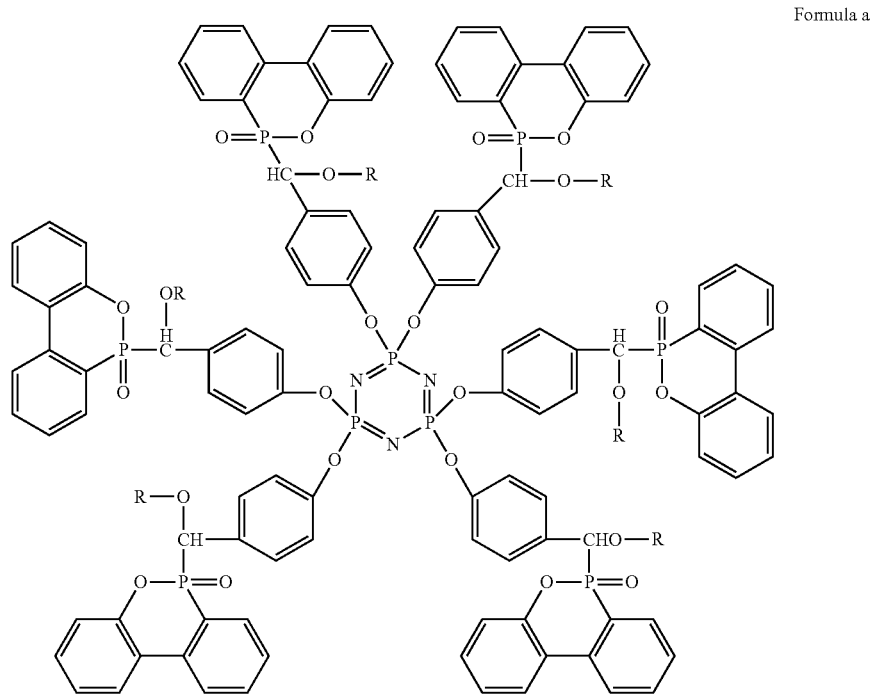
Formula a
wherein six Rs in Formula a are each independently
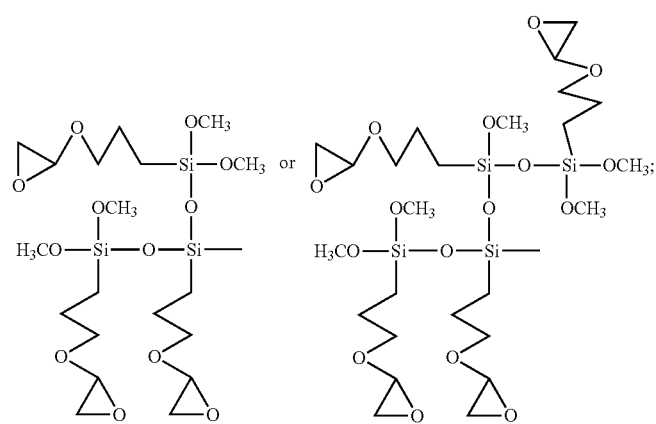

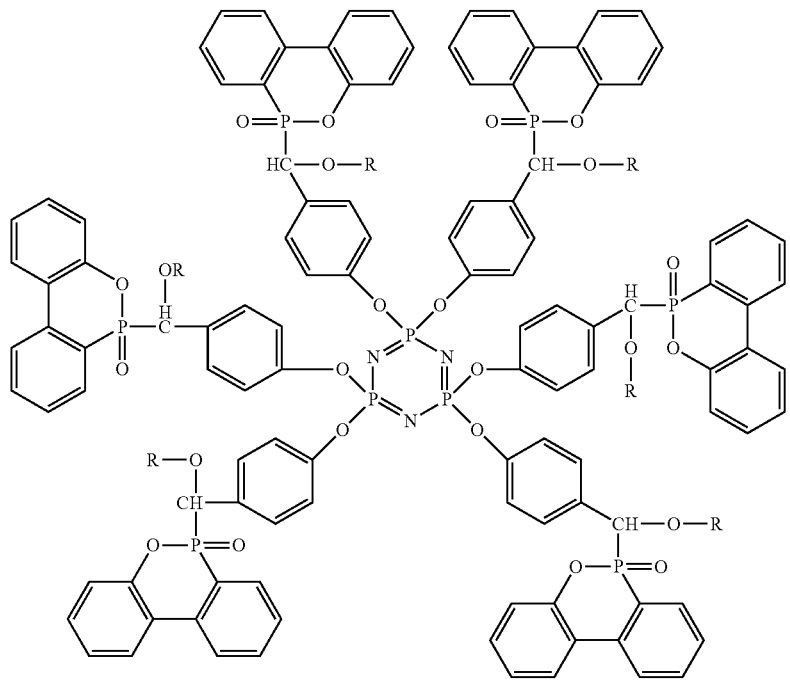
Formula b
wherein six Rs in Formula b are each independently
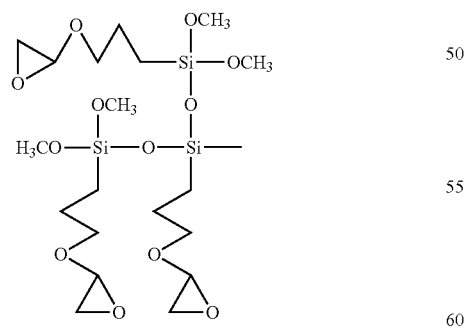
or H, but not H at the same time;

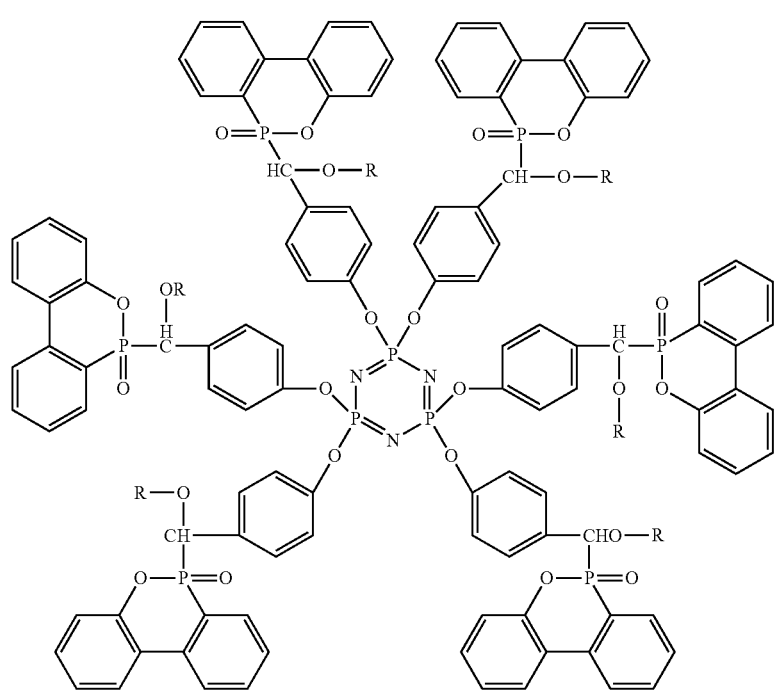
Formula c
wherein six Rs in Formula c are each independently
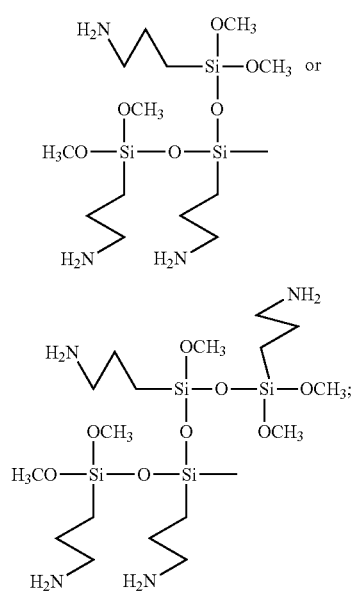
-continued
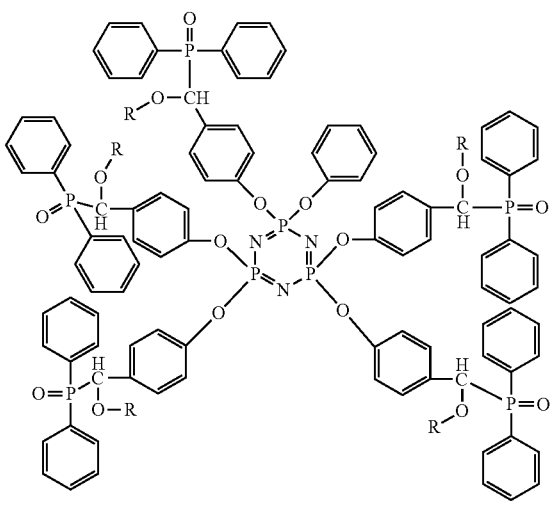
Formula d wherein six Rs in Formula d are each independently
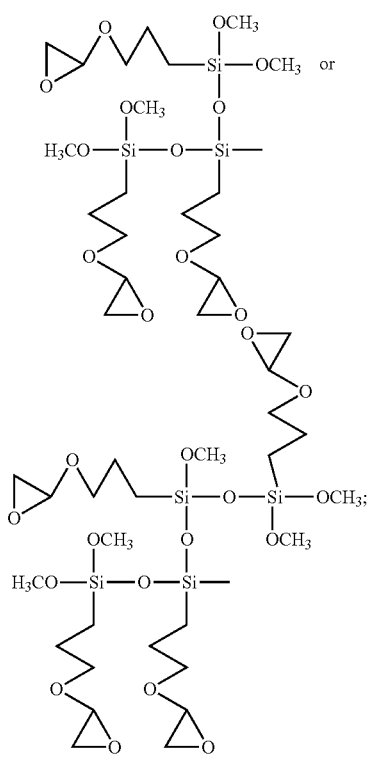 or
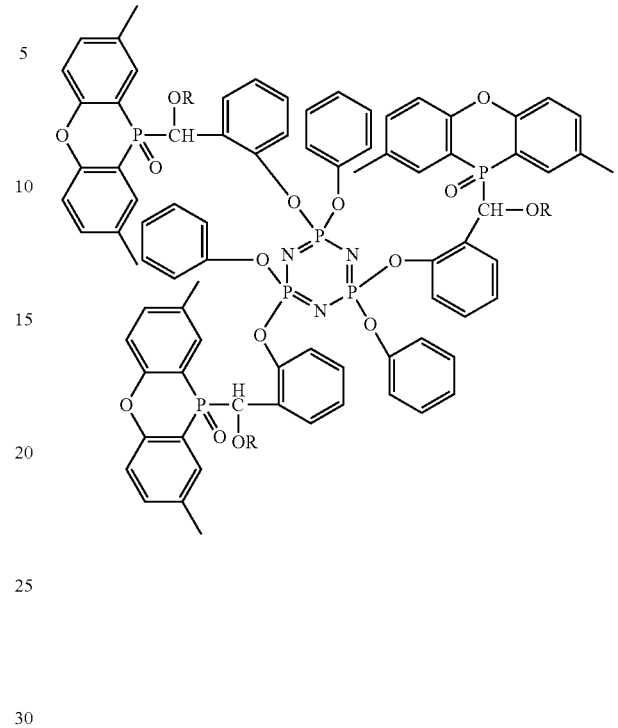
wherein Rs in Formulae are
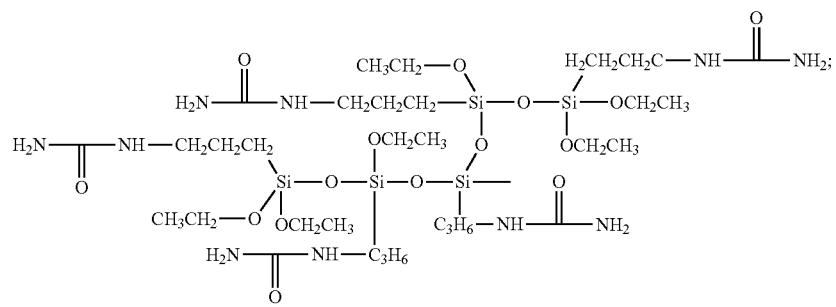
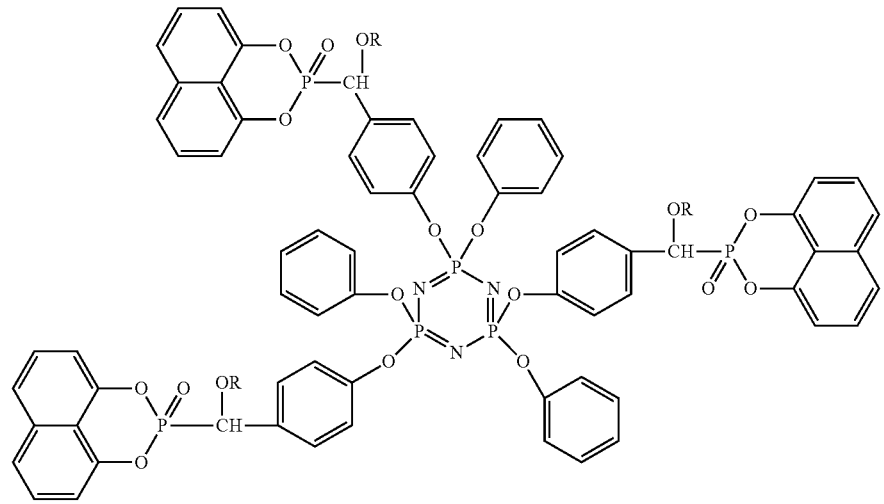

wherein three Rs in Formula f are each independently

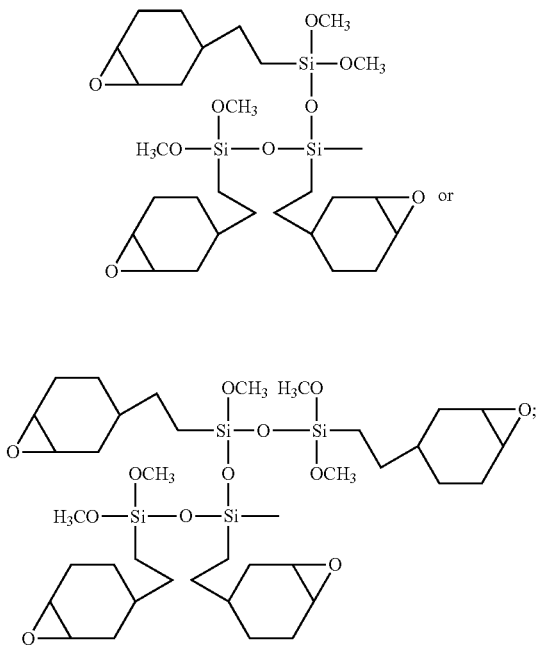

or

Formula g wherein three Rs in Formula g are each independently

7. A process for preparing the siloxane-modified cyclotriphosphazene halogen free flame retardant according to claim 1, wherein the process comprises the following steps:

(1) reacting aldehyde- or keto-substituted aryl phenol shown in Formula II and any optional aryl phenol shown in Formula III with hexachlorocyclotriphosphazene to obtain the cyclotriphosphazene compound as shown in Formula IV, wherein the reaction formula is as follows:

(2) reacting the cyclotriphosphazene compound as shown in Formula IV obtained in step (1) with phosphorus-containing aromatic compound containing P—H bonds as shown in Formula V to obtain the cyclotriphosphazene compound containing hydroxyl and aryl phosphorus oxygen structure as shown in Formula VI, wherein the reaction formula is as follows:

-continued

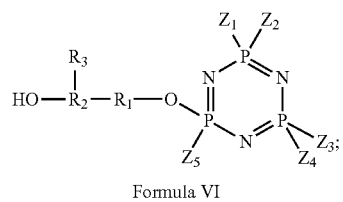

Formula VI (3) reacting the cyclotriphosphazene compound containing hydroxyl and aryl phosphorus oxygen structure as shown in Formula VI obtained in step (2) with siloxane monomer as shown in Formula VII to obtain the siloxane-modified cyclotriphosphazene halogen-free flame retardant as shown in Formula I, wherein the reaction formula is as follows:

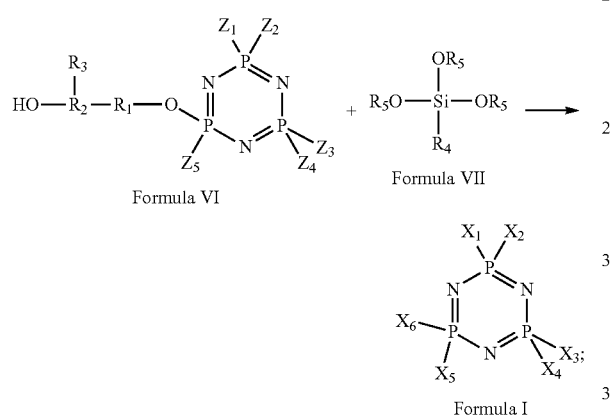

wherein the groups of $Y_1$-$Y_5$ are each independently selected from $R_6$—$R_1$—O— and —O—R', and at least one is $R_6$—$R_1$—O—; $R_1$ is a substituted or unsubstituted arylidene; $R_6$ is aldehyde group or

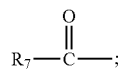

$R_7$ is a substituted or unsubstituted C1-C5 alkyl or a substituted or unsubstituted aryl; R' is a substituted or unsubstituted aryl; the groups of $Z_1$-$Z_5$ are each independently selected from

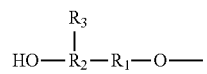

or —O—R', and at least one is

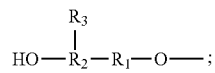

$R_2$ is selected from the group consisting of methenyl,

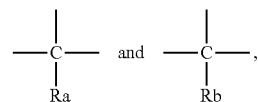

wherein $R_a$ is a substituted or unsubstituted C1-C5 alkyl; $R_b$ is a substituted or unsubstituted aryl; $R_3$ is a group containing aryl phosphorus oxygen structure; the groups of $X_1$-$X_6$ are each independently selected from

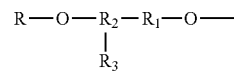

or —O—R', and at least two groups are

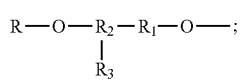

$R_4$ is selected from the group consisting of

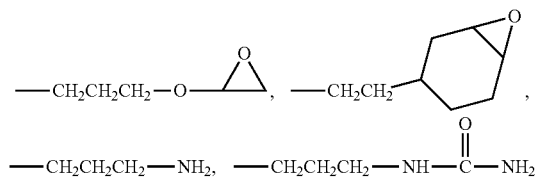

and —$CH_2CH_2CH_2$—NH—$CH_2CH_2$—$NH_2$; $R_5$ is selected from the group consisting of C1-C5 alkyl groups; R' is a substituted or unsubstituted aryl; Rs in $X_1$-$X_6$ are independently selected from siloxane group or hydrogen, and Rs in $X_1$-$X_6$ are not hydrogen at the same time.

8. The process according to claim 7, wherein
during the reaction of the mixture of aldehyde- or keto-substituted aryl phenol shown in Formula II and aryl phenol shown in Formula III with hexachlorocyclotriphosphazene in step (1), the aldehyde- or keto-substituted aryl phenol shown in Formula II and aryl phenol shown in Formula III are in a molar ratio of 1:2-10:1;
in step (1), the two of the aldehyde- or keto-substituted aryl phenol shown in Formula II and aryl phenol shown in Formula III and hexachlorocyclotriphosphazene are in a molar ratio of 6.1:1-7.1:1;
the aldehyde- or keto-substituted aryl phenol shown in Formula II in step (1) is selected from the group consisting of

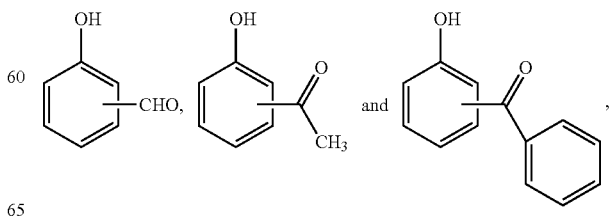

or a combination of at least two selected therefrom;

the aryl phenol shown in Formula III in step (1) is selected from the group consisting of

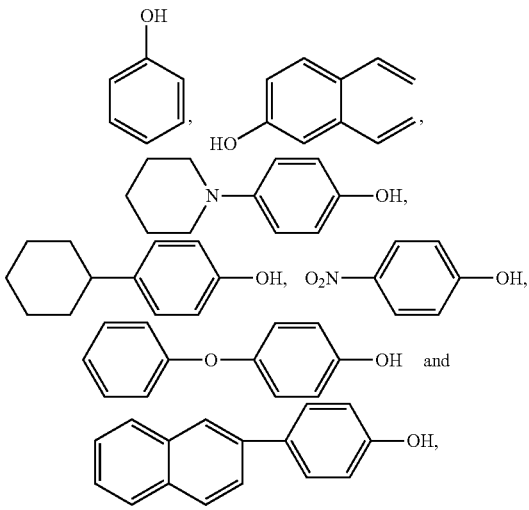

or a combination of at least two selected therefrom.

9. The process according to claim 7, wherein the reaction in step (1) is carried out in an aprotic organic solvent having a boiling point of lower than 105° C.;
the reaction in step (1) is carried out in a reflux for 20-36 h;
the aldehyde- or keto-substituted aryl phenol shown in Formula II and any optional aryl phenol shown in Formula III are reacted with an acid-binding agent at room temperature before the reaction in step (1) for 1-5h;
the acid-binding agent and the aldehyde- or keto-substituted aryl phenol shown in Formula II and any optional aryl phenol shown in Formula III are in a molar ratio of 1.1:1-1.3:1.

10. The process according to claim 7, wherein the phosphorus-containing aromatic compound containing P—H bonds as shown in Formula V in step (2) is selected from the group consisting of diphenylphosphine oxide, 9,10-dihydro-9-oxa-10-phosphaphenanthrene-10-oxide, 1,8-dinaphthyl-1,3,2-dioxaphosphine and 9,10-dihydro-9-oxa-10-phosphaanthracene-10-oxide, or a combination of at least two selected therefrom;
in step (2), the cyclotriphosphazene compound of Formula IV and the phosphorus-containing compound containing P—H bonds of Formula V have a molar ratio of 1:2-1:6.3;
the reaction in step (2) is carried out in an aprotic organic solvent having a boiling point of higher than 150° C.;
the reaction temperature in step (2) ranges from 130-175° C.;
the reaction in step (2) lasts for 8-20 h.

11. The process according to claim 7, wherein the siloxane monomer of Formula VII in step (3) is selected from the group consisting of γ-(2,3-epoxypropoxy)propyltrimethoxy silane, γ-(2,3-epoxypropoxy)propyltriethoxysilane, 2-(3,4-epoxycyclohexyl)ethyltriethoxy silane, 3-ureidopropyltriethoxysilane, γ-aminopropyltriethoxy-silane and N-(2-aminoethyl)-3-aminopropyltriethoxysilane, or a combination of at least two selected therefrom;
the cyclotriphosphazene compound containing hydroxyl and aryl phosphorus oxygen structure as shown in Formula VI and the siloxane monomer as shown in Formula VII have a molar ratio of 1:1-4:1;
the reaction in step (3) is carried out in the presence of a catalyst;
the catalyst is selected from the group consisting of zinc isooctanoate, dibutyltin dilaurate, iron isooctanoate, manganese isooctanoate, cobalt isooctanoate, zirconium isooctanoate, cobalt acetylacetonate and copper acetylacetonate, or a combination of at least two selected therefrom;
the catalyst is used in an amount of 0.1-0.8% by mass of the siloxane monomer as shown in Formula VII;
the step (3) is carried out in the presence of deionized water;
the deionized water and the siloxane groups in the siloxane monomer as shown in the Formula VII have a molar ratio of 0.7:1-1.3:1;
the reaction in step (3) is carried out at 70-90° C. for 5-7 h, and continues at 110-140° C. for 3-5 h.

12. The process according to claim 7, wherein the reactions in steps (1)-(3) are carried out in the presence of a protecting gas; wherein the protecting gas is nitrogen.

13. A halogen-free flame retardant resin composition, wherein the halogen-free flame retardant resin composition comprises the siloxane-modified cyclotriphosphazene halogen-free flame retardant as claimed in claim 1.

14. The halogen-free flame retardant resin composition according to claim 13, wherein the siloxane-modified cyclotriphosphazene halogen-free flame retardant is in an amount of 7-22% by weight of the halogen-free flame retardant resin composition.

15. A prepreg prepared by using the halogen-free flame retardant resin composition claimed in claim 14.

16. The halogen-free flame retardant resin composition according to claim 13, wherein the halogen-free flame retardant resin composition further comprises other thermosetting resins; wherein the other thermosetting resin is selected from the group consisting of epoxy resin, unsaturated resin, polyurethane, cyanate resin and benzoxazine resin, or a combination of at least two selected therefrom.

17. The halogen-free flame retardant resin composition according to claim 13, wherein the halogen-free flame retardant resin composition further comprises a curing agent;
wherein the curing agent is selected from the group consisting of phenolic curing agent, amine curing agent, anhydride curing agent, active ester and free radical initiator, or a combination of at least two selected therefrom.

18. The halogen-free flame retardant resin composition according to claim 13, wherein the halogen-free flame retardant resin composition further comprises a filler;
wherein the filler is selected from the group consisting of silica, alumina, titania, barium titanate, strontium titanate, magnesium titanate, calcium titanate, barium strontium titanate, lead titanate and glass powder, or a combination of at least two selected therefrom.

19. A resin glue, wherein the resin glue is obtained by dissolving or dispersing the halogen-free flame retardant resin composition claimed in claim 13 in a solvent.

20. The resin glue according to claim 19, wherein the solvent is one selected from the group consisting of ketones, hydrocarbons, ethers, esters and aprotic solvents, or a combination of at least two selected therefrom.

21. A prepreg prepared by using the halogen-free flame retardant resin composition claimed in claim 13.

22. A metal-clad laminate, wherein the metal-clad laminate comprises one or at least two superimposed prepregs and metal foil located on one or both sides of the prepreg.

* * * * *